United States Patent
Posner et al.

(10) Patent No.: US 6,982,258 B2
(45) Date of Patent: Jan. 3, 2006

(54) LOW-CALCEMIC OXIME ANALOGS OF 1α, 25-DIHYDROXY VITAMIN $D_3$

(75) Inventors: Gary Posner, Baltimore, MD (US); Mehmet Kahraman, Baltimore, MD (US); Heung Bae Jeon, Baltimore, MD (US); Jay A. White, Ontario (CA); Glenville Jones, Ontario (CA); Bethany Halford, Baltimore, MD (US)

(73) Assignees: Cytochroma Inc., Markham (CA); Johns Hopkins University, Baltimore, MD (US)

( * ) Notice: Subject to any disclaimer, the term of this patent is extended or adjusted under 35 U.S.C. 154(b) by 121 days.

(21) Appl. No.: 10/270,158

(22) Filed: Oct. 15, 2002

(65) Prior Publication Data

US 2003/0171342 A1 Sep. 11, 2003

Related U.S. Application Data

(60) Provisional application No. 60/328,428, filed on Oct. 12, 2001.

(51) Int. Cl.
*A61K 31/593* (2006.01)
*C07C 401/00* (2006.01)

(52) U.S. Cl. ........................................ 514/167; 552/653
(58) Field of Classification Search ................ 514/167; 552/653
See application file for complete search history.

(56) References Cited

U.S. PATENT DOCUMENTS

4,481,198 A  11/1984  DeLuca et al.

FOREIGN PATENT DOCUMENTS

WO  98/21580  *  5/1998

OTHER PUBLICATIONS

Boyan, B. D. et al., "1,25-(OH)$_2$D$_3$ Modulates Growth Plate Chondrocytes via Membrane Receptor–Mediated Protein Kinase C by a Mechanism That Involves Changes in Phospholipid Metabolism and the Action of Arachidonic Acid and PGE$_2$", Steroids, 1999, vol. 64, pp. 129–136.

Crawford, K. R., "Design, Synthesis, and Preliminary Biological Evaluation of Analogs of 1α,25–Dihydroxyvitamin D$_3$: Modifications to the A–Ring and C,D–Ring Side Chain", Ph.D. Thesis, Johns Hopkins University, 2001, pp. 13–16, 51–55.

Dai, H. et al., "Synthetic Approahces to Vitiman D", Synthesis, Dec. 1994, pp. 1383–1398.

Greising, D. M. et al., "A–Ring Analogues of 1,25–(OH)$_2$D$_3$ With Low Affinity for the Vitamin D Receptor Modulate Chondrocytes via Membrane Effects That Are Dependent on Cell Maturation", Journal of Cellular Physiology, 1997, vol. 171, pp. 357–367.

Guyton, K. Z. et al., "Cancer Chemoprevention Using Natural Vitamin D and Synthetic Analogs", Annu. Rev. Pharmacol. Toxicol., 2001, vol. 41, pp. 421–442.

Guyton, K. Z. et al., "Vitamin D and Vitamin D Analogs as Cancer Chemopreventive Agents", Nutrition Reviews, 2003, vol. 61, No. 7, pp. 1–12.

Haidar, S. et al., Synthesis and Evaluation of Steroidal Hydroxamic Acids as Inhibitors of P450 17(17α–Hydroxylase/C17–20–Lyase), Arch. Pharm. Pharm. Med. Chem. 2001, vol. 334, pp. 138–140.

Hartmann, R. W. et al., "Synthesis and Evaluation of Novel Steroidal Oxime Inhibitors of P450 17(17α–Hydroxylase/C17–20–Lyase) and 5–α–Reductase Types 1 and 2", J. Med. Chem., 2000, vol. 43, pp. 4266–4277.

Hatcher, M. A. et al., "[3,3]–Sigmatropic Rearrangements: Short, Stereocontrolled Syntheses of Functionalized Vitamin D$_3$ Side–chain Units", Tetrahedron Letters, 2002, vol. 43, pp. 5009–5012.

Hilpert, H. et al., "Novel Versatile Approach to an Enantiopure 19–nor,des–C,D Vitamin D$_3$ Derivative", Tetrahedron, 2001, vol. 57, pp. 681–694.

Hofer, H. et al., "Biological Effects of 1α–Hydroxy– and 1β–(Hydroxymethyl)–Vitamin D Compounds Relevant for Potential Colorectal Cancer Therapy", The Journal of Pharmacology and Experimental Theraputics, 1999, vol. 291, No. 2, pp. 450–455.

Kensler, T. W. et al., "Conceptually New Deltanoids (Vitamin D Analogs) Inhibit Multistage Skin Tumorigenesis", Carcinogenesis, 2000, vol. 21, No. 7, pp. 1341–1345, XP–001121614.

Peleg, S. et al., "Vitamin D Analogs as Modulators of Vitamin D Receptor Action", Current Topics in Medicinal Chemistry, 2003, vol. 3, No. 8, pp. 1–20.

Peleg, S. et al., "A 20–Epi Side Chain Restores Growth––Regulatory and Transcriptional Activities of an A Ring–Modified Hybrid Analog of 1α,25–Dihydroxyvitamin $D_3$ Without Increasing Its Affinity to the Vitamin D Receptor", Journal of Cellular Biochemistry, 1996, vol. 63, pp. 149–161.

Peleg, S. et al., "Differential Use of Transcription Activation Function 2 Domain of the Vitamin D Receptor by 1,25–Dihydroxyvitamin $D_3$ and Its A Ring–Modified Analogs", Molecular Endocrinology, 1998, vol. 12, No. 4, pp. 525–535.

Posner, G. H. et al., "1α,25–Dihydroxyvitamin $D_3$ Analogs Featuring Aromatic and Heteroaromatic Rings: Design, Synthesis, and Preliminary Biological Testing", J. Med. Chem., 1995, vol. 38, pp. 4529–4537.

Posner, G. H. et al., "1α,25–Dihydroxyvitamin $D_3$ Hybrid Analogs with Structural Changes at Both the A–Ring and the C,D–Ring Side–chain", Bioorganic & Medicinal Chemistry Letters, 1994, vol. 4, No. 24, pp. 2919–2924.

Posner, G. H. et al., "1α,25–Dihydroxyvitamin $D_3$ Hybrid Analogs with Structural Changes at Both the A–Ring and the C,D–Ring Side–chain. II", Bioorganic & Medicinal Chemistry Letters, 1995, vol. 5, No. 18, pp. 2163–2168.

Posner, G. H. et al., "2,2–Disubstituted Analogues of the Natural Hormone 1α,25–Dihydroxyvitamin $D_3$: Chemistry and Biology", Bioorganic & Medicinal Chemistry, 2002, vol. 10, pp. 2353–2365.

Posner, G. H. et al., "2–Fluoroalkyl A–Ring Analogs of 1α,25–Dihydroxyvitamin $D_3$. Stereocontrolled Total Synthesis via Intramolecular and Intermolecular Diels–Alder Cycloadditions. Preliminary Biological Testing", J. Org. Chem., 1995, vol. 60, No. 14, pp. 4617–4628.

Posner, G. H. et al., "A Non–Calcemic Sulfone Version of the Vitamin $D_3$ Analogue Seocalcitol (EB 1089): Chemical Synthesis, Biological Evaluation and Potency Enhancement of the Anticancer Drug Adriamycin", Bioorganic & Medicinal Chemistry, 2001, vol. 9, pp. 2365–2371.

Posner, G. H., et al., "Antiproliferative Hybrid Analogs of the Hormone 1α,25–Dihydroxyvitamin $D_3$: Design, Synthesis, and Preliminary Biological Evaluation", J. Org. Chem., 1997, vol. 62, pp. 3299–3314.

Posner, G. H. et al., "Conceptually New Low–Calcemic Oxime Analogues of the Hormone 1α,25–Dihydroxyvitamin $D_3$: Synthesis and Biological Testing", J. Med. Chem., 2002, vol. 45, pp. 1723–1730.

Posner, G. H. et al., "Conceptually New Low–Calcemic Oxime Analogues of the Hormone 1α,25–Dihydroxyvitamin $D_3$: Synthesis and Biological Testing", J. Med. Chem., 2002, vol. 45, No. 8, pp. 1723–1730, XP–002229473.

Posner, G. H. et al., "Conceptually New 20–epi–22–Oxa Sulfone Analogues of the Hormone 1α,25–Dihydroxyvitamin $D_3$: Synthesis and Biological Evaluation", Journal of Medicinal Chemistry, 2000, vol. 43, No. 19, pp. 3581–3586.

Posner, G. H. et al., "Conceptually New Sulfone Analogues of the Hormone 1α,25–Dihydroxyvitamin $D_3$: Synthesis and Biological Evaluation", Journal of Medicinal Chemistry, 1999, vol. 42, No. 18, pp. 3425–3435.

Posner, G. H., "New Vitamin D Analogues", Nephrol Dial Transplant, 1996, vol. 11, Suppl. 3, pp. 32–36.

Posner, G. H. et al., "New Vitamin $D_3$ Derivatives with Unexpected Antiproliferative Activity: 1–(Hydroxymethyl)–25–hydroxyvitamin $D_3$ Homologs", J. Med. Chem., 1992, vol. 35, No. 17, pp. 3280–3287.

Posner, G. H. et al., "Noncalcemic Antiproliferative, Transcriptionally Active, 24–Fluorinated Hybrid Analogues of the Hormone 1α,25–Dihydroxyvitamin $D_3$. Synthesis and Preliminary Biological Evaluation" Journal of Medicinal Chemistry, 1998, vol. 41, No. 16, pp. 3008–3014.

Posner, G. H. et al., "Stereocontrolled Synthesis of a Trihydroxylated A Ring as an Immediate Precursor to 1α,2α,25–Trihydroxyvitamin $D_3$", J. Org. Chem., 1991, vol. 56, No. 14, pp. 4339–4341.

Posner, G. H. et al., "Stereocontrolled Total Synthesis of Calcitriol Derivatives; 1–25–Dihydroxy–2–(4'–hydroxybutyl) Vitamin $D_3$ Analogs of an Osteoporosis Drug", J. Org. Chem., 1994, vol. 59, No. 25, pp. 7855–7861.

Posner, G. H. et al., "Vitamin D Endocrine System— Structural, Biological, Genetic and Clinical Aspects", Proceedings of the Eleventh Workshop on Vitamin D, Nashville, Tennessee, USA, May 27–Jun. 1, 2000, pp. 3–10.

Schuster, I. et al., "Selective Inhibition of Vitamin D Hydroxylases in Human Keratinocytes", Steroids, 2001, vol. 66, pp. 409–422, XP–002229474.

Wang, Q., "Noncalcemic, Antiproliferative, Transcriptionally Active Hybrid Analogs of the Hormone 1α,25–Dihydroxyvitamin $D_3$: Design, Synthesis, and Preliminary Biological Evaluation", Ph.D. Thesis, Johns Hopkins University, 2000, pp. 39–57.

* cited by examiner

Primary Examiner—Sabiha Qazi
(74) Attorney, Agent, or Firm—Rothwell Figg Ernst & Manbeck

(57) ABSTRACT

The present invention provides novel 16-ene-C25-oxime and 16-ene-C-25-oxime ether analogs of 1α,25-dihydroxy vitamin $D_3$, compositions comprising these compounds and methods of using these compounds as inhibitors of CYP24. In particular, the compound of Formula I are useful for treating diseases which benefit from a modulation of the levels of 1α,25-dihydroxy vitamin $D_3$, for example, cell-proliferative disorders.

42 Claims, 6 Drawing Sheets

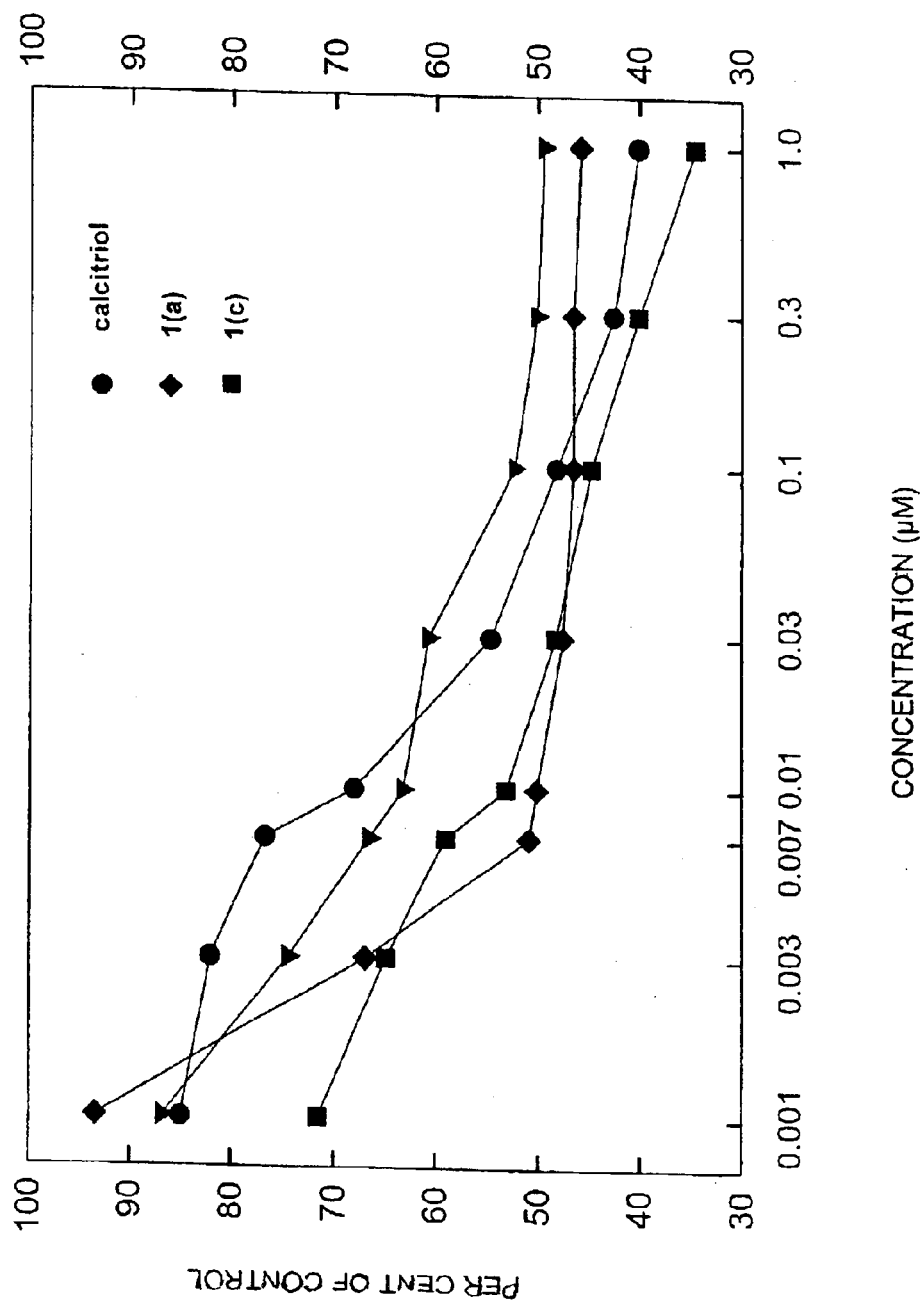

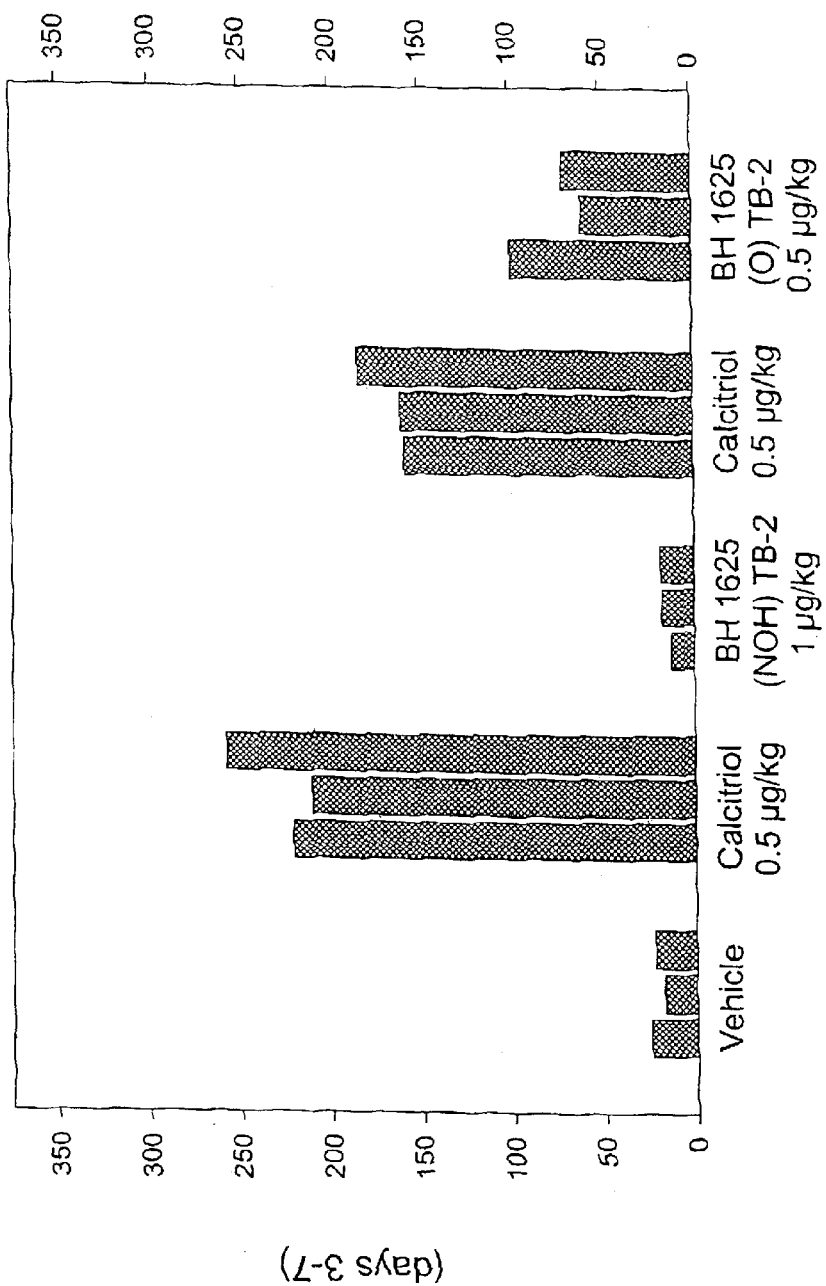

LOW-CALCEMIC OXIME ANALOGS OF 1α, 25-DIHYDROXY VITAMIN D₃

CROSS REFERENCE TO RELATED APPLICATIONS

This application claims the benefit under 35 USC §119(e) from U.S. provisional patent application Ser. No. 60/328,428, filed Oct. 12, 2001, the contents of which are incorporated herein by reference in their entirety.

This invention was made with government support under NIH Grant Number CA 44530. The government has certain rights in the invention.

FIELD OF THE INVENTION

The present invention relates to novel analogs of the hormone 1α,25-dihydroxy vitamin $D_3$ that show selective inhibition of the enzyme CYP24 and which are low-calcemic and anti-proliferative, to pharmaceutical and diagnostic compositions containing them and to their medical use, particularly in the treatment and/or prevention of cancer, dermatological disorders, bone disorders, thyroid disorders, wound healing and osteoporosis.

BACKGROUND OF THE INVENTION

The vitamin D metabolic pathway is part of a vital endocrine system that is highly regulated at certain stages and produces metabolites that control the secretion of the parathyroid gland hormones (Beckman, M., and DeLuca, H. (1997) *Methods in Enzymol.* 282, 200–223; Jones, G., Strugnell, S., and DeLuca, H. (1998) *Physiol. Rev.* 78, 1193–1231). 1α,25-Dihydroxy vitamin $D_3$, also known as calcitriol (see below), a hormone produced in the vitamin D pathway, regulates phosphate and calcium levels in the blood which in turn control bone mass, the state of bones, and affects cellular differentiation in the skin and the immune system (Armbrecht, H. J., Okuda, K., Wongsurawat, N., Nemani, R., Chen, M., and Boltz, M. (1992) *J. Steroid Biochem. Molec. Biol.* 43, 1073–1081). In the vitamin D pathway, cytochrome P450s are enzymes that introduce functional groups by hydroxylation, usually at positions 1, 25, and 24, of vitamin $D_3$ (Beckman, M., and DeLuca, H. (1997) *Methods in Enzymol.* 282, 200–223).

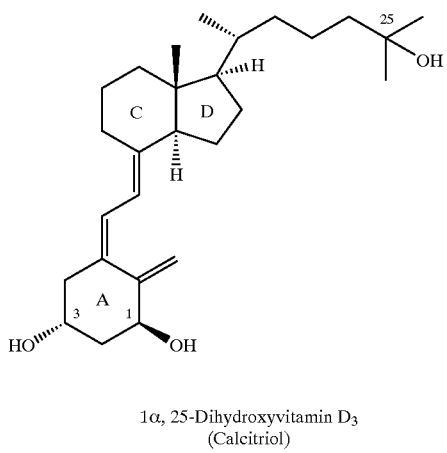

1α, 25-Dihydroxyvitamin $D_3$
(Calcitriol)

1α,25-Dihydroxy vitamin $D_3$ is converted to 1α,24,25-trihydroxy-$D_3$ by a mitochondrial P450 known as CYP 24 (Bell, N. H., (1998) *J. Bone Miner. Res.* 13, 350–35211). CYP 24 is induced by 1α,25-dihydroxy-$D_3$ and is found in the kidney as well as other vitamin D target tissues such as the parathyroid cells, keratinocytes, osteoblasts, and enteroctyes (Jones, G., Strugnell, S., and DeLuca, H. (1998) *Physiol. Rev.* 78, 1193–1231). 1α, 25-Dihydroxy vitamin $D_3$ (1,25-D3) has an important role in the antiproliferative and growth regulatory effects on normal and neoplastic cells (for e.g. prostate cancer cells). Clinical use of 1,25-D3 analogs as effective drugs requires antiproliferative and pro-differentiating activities. There is a continuing need for synthetic analogs of 1α,25-dihydroxy vitamin $D_3$ that selectively exhibit desirable pharmacological activities but do not exhibit hypercalcemic and other undesirable activities.

SUMMARY OF THE INVENTION

Novel 16-ene-25-oxime and 16-ene-25-oxime ether analogs of 1α,25-dihydroxy vitamin $D_3$ have been prepared that show selective inhibition of the enzyme CYP24, antiproliferative activity and are low-calcemic.

The present invention therefore provides compounds of Formula I, and pharmaceutically acceptable salts, hydrates, solvates, and prodrugs thereof:

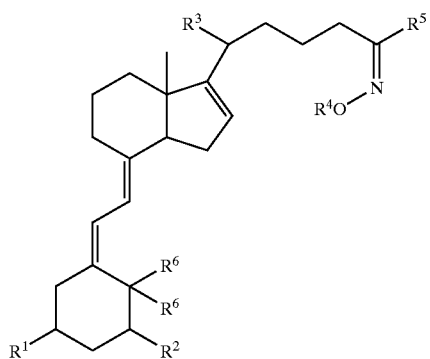

I wherein
$R^1$ and $R^2$ are independently selected from the group consisting of OH, $OC_{1-6}$alkyl, and halo;
$R^3$ is $C_{1-6}$alkyl;
$R^4$ is selected from the group consisting of H, $C_{1-6}$alkyl, aryl and heteroaryl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with aryl and heteroaryl being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, C(O)$OC_{1-4}$alkyl, C(O)$NHC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$;
$R^5$ is selected from the group consisting of $C_{1-6}$alkyl, cyclo($C_3$–$C_6$)alkyl, aryl, heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with cyclo($C_3$–$C_6$)alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, C(O)$OC_{1-4}$alkyl, C(O)$NHC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$; and
$R^6$ are either both H or together form $=CH_2$.

Preferably, the compounds of the invention have the stereochemistry of natural 1α,25-dihydroxy vitamin $D_3$. Therefore, in a preferred embodiment, the present invention provides compounds of Formula I, and pharmaceutically acceptable salts, hydrates, solvates, and prodrugs thereof, as shown below:

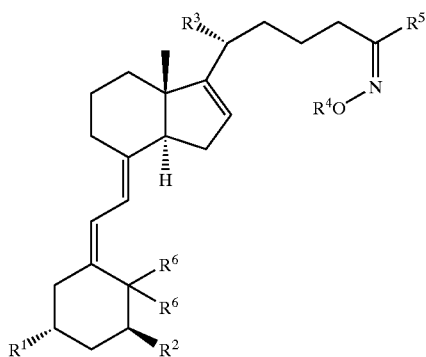

I wherein
$R^1$–$R^6$ are as defined above.

According to another aspect of the present invention, there is provided a pharmaceutical composition comprising a compound of Formula I and a pharmaceutically acceptable carrier or diluent.

By selectively modulating CYP24, the enzyme that metabolizes 1α,25-dihydroxy vitamin $D_3$, the levels of 1α,25-dihydroxy vitamin $D_3$ are also modulated. Diseases that benefit from a modulation of the levels of 1α,25-dihydroxy vitamin $D_3$ can therefore be treated using a modulator of CYP24. By acting preferentially on CYP24, side effects caused by interaction with other enzymes and receptors will be reduced. Accordingly, the present invention provides a method for treating diseases which benefit from a modulation of the levels of 1α,25-dihydroxy vitamin $D_3$ comprising administering an effective amount of a compound of Formula I to a cell or animal in need thereof. The invention also includes the use of a compound of Formula I to modulate the levels of 1α,25-dihydroxy vitamin $D_3$. Further, the invention includes a use of a compound of Formula I to prepare a medicament to modulate the levels of 1α,25-dihydroxy vitamin $D_3$.

Inhibition of CYP24, inhibits the catabolism of 1α,25-dihydroxy vitamin $D_3$ which will lengthen the biological lifetime of this hormone and thus allow smaller amounts of it to be used for effective disease treatment. Such smaller dosing will avoid, or at least minimize, the hypercalcemic toxicity associated with medicinal use of 1α,25-dihydroxy vitamin $D_3$ (calcitriol). Therefore, in an embodiment, the present invention provides a method for treating diseases which benefit from inhibiting the catabolism of 1α,25-dihydroxy vitamin $D_3$ comprising administering an effective amount of a compound of Formula I to a cell or animal in need thereof. The invention also includes the use of a compound of Formula I to inhibit the catabolism of 1α,25-dihydroxy vitamin $D_3$. Further, the invention includes a use of a compound of Formula I to prepare a medicament to inhibit the catabolism of 1α,25-dihydroxy vitamin $D_3$.

Diseases which may benefit for a modulation in the levels of 1α,25-dihydroxy vitamin $D_3$ include, but are not limited to:

(i) in the parathyroid—hyper- and hypo-parathyroidism, Pseudohypoparathyroidism, Secondary hyperparathyroidism;

(ii) in the pancreas—diabetes;
(iii) in the thyroid—medullary carcinoma;
(iv) in the skin—psoriasis, wound healing;
(v) in the lung—sarcoidosis and tuberculosis;
(vi) in the kidney—chronic renal disease, hypophosphatemicVDRR, vitamin D dependent rickets;
(vii) in the bone—anticonvulsant treatment, fibrogenisis imperfecta ossium, osteitits fibrosa cystica, osteomalacia, osteoporosis, osteopenia, osteosclerosis, renal osteodytrophy, rickets;
(viii) in the intestine—glucocorticoid antagonism, idopathic hypercalcemia, malabsorption syndrome, steatorrhea, tropical sprue.

The compounds of Formula I, or salts, solvates, hydrates or prodrugs thereof, can be used alone or in combination with other agents that modulate CYP24 activity or in combination with other types of treatment (which may or may not modulate CYP24) for cell proliferative disorders or other disorders that benefit from a modulation in the levels of 1α,25-dihydroxy vitamin D and/or an inhibition of the catabolism of 1α,25-dihydroxy vitamin $D_3$. Preferably the compounds of Formula I are administered in combination with 1α,25-dihydroxy vitamin D (calcitrol) or other vitamin D receptor agonists. The present invention therefore provides a method of increasing the efficacy of a vitamin D receptor agonist, preferably 1α,25-dihydroxy vitamin $D_3$ (calcitriol), comprising co-administering an effective amount of a compound of Formula I and an effective amount of the vitamin D receptor agonist, preferably 1α,25-dihydroxy vitamin $D_3$ (calcitriol). Further the invention includes a use of a compound of Formula I to increase the efficacy of a vitamin D receptor agonist, preferably 1α,25-dihydroxy vitamin $D_3$ (calcitriol), and a use of a compound of Formula I to prepare a medicament to increase the efficacy of a vitamin D receptor agonist, preferably 1α,25-dihydroxy vitamin $D_3$ (calcitriol).

In accordance with a further aspect of the present invention, there is provided a method for modulating cell proliferation, preferably inhibiting cell proliferation, comprising administering an effective amount of a compound of Formula I to a cell or animal in need thereof. The invention also includes a use of a compound of Formula I to modulate cell proliferation, preferably to inhibit cell proliferation. The invention further includes a use of a compound of Formula I to prepare a medicament to modulate cell proliferation, preferably to inhibit cell proliferation.

In an embodiment, the present invention provides a method of inhibiting the proliferation of a cancer cell comprising administering an effective amount of a compound of Formula I to a cell or animal in need thereof. The invention also includes a use of a compound of Formula I to inhibit cancer cell proliferation. The invention further includes a use of a compound of Formula I to prepare a medicament to inhibit cancer cell proliferation.

In another aspect, the invention provides a method of modulating CYP24 activity in a cell or animal by administering an effective amount of a compound of Formula I. In a further aspect, the invention provides a method of modulating CYP24 activity, preferably inhibiting CYP24 activity by administering an effective amount of a compound of Formula I to a cell or animal in need thereof. The present invention also provides a use of a compound of Formula I to modulate, preferably to inhibit, CYP24 activity. The present invention further provides a use of a compound of Formula I to prepare a medicament to modulate CYP24 activity, preferably to inhibit CYP24 activity. It is appreciated that the inhibition of cell growth by the compounds of the invention may be effected by other mechanisms.

The present invention further provides novel compounds useful in the preparation of the compounds of Formula I. Therefore the present invention further provides compounds of Formula II, and salts, hydrates and solvates thereof:

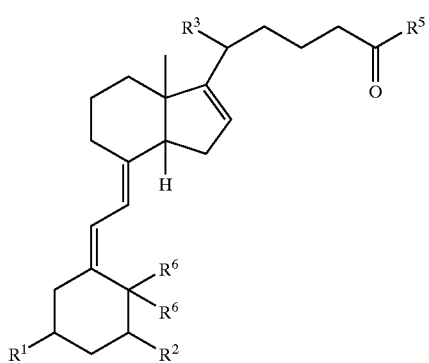

wherein
$R^1$ and $R^2$ are independently selected from the group consisting of OH, $OC_{1-6}$alkyl, OPG and halo;
PG is a protecting group;
$R^3$ is $C_{1-6}$alkyl;
$R^5$ is selected from the group consisting of $C_{1-6}$alkyl, cyclo($C_3$–$C_6$)alkyl, aryl, heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with cyclo($C_3$–$C_6$)alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)$OC_{1-4}$alkyl, C(O)$NHC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$; and
$R^6$ are either both H or together form $=CH_2$.

Further, the present invention provides a method for preparing a compound of Formula I comprising reacting a compound of Formula II, or a salt, hydrate or solvate thereof, with a compound of Formula III, or a salt hydrate of solvate thereof:

 $NH_2$—$OR^4$                                III, wherein $R^4$ is selected from the group consisting of H, $C_{1-6}$alkyl, aryl and heteroaryl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with aryl and heteroaryl being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)$OC_{1-4}$alkyl, C(O)$NHC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$,
in the presence of non-nucleophilic amine, followed by removal of any protecting groups, if present.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 5 is a graph showing the dose response effects of compounds I(a) and I(c) on keratinocyte proliferation in comparison to 1α,25-Dihydroxy vitamin $D_3$ or calcitriol.

FIG. 6 is a graph showing the effect of compounds I(a) (indicated as BH 1625(NOH)) on calcium levels in rat urine in comparison to calcitriol (1α,25-Dihydroxy vitamin $D_3$).

DETAILED DESCRIPTION OF THE INVENTION

I. Definitions

Figure 1A:
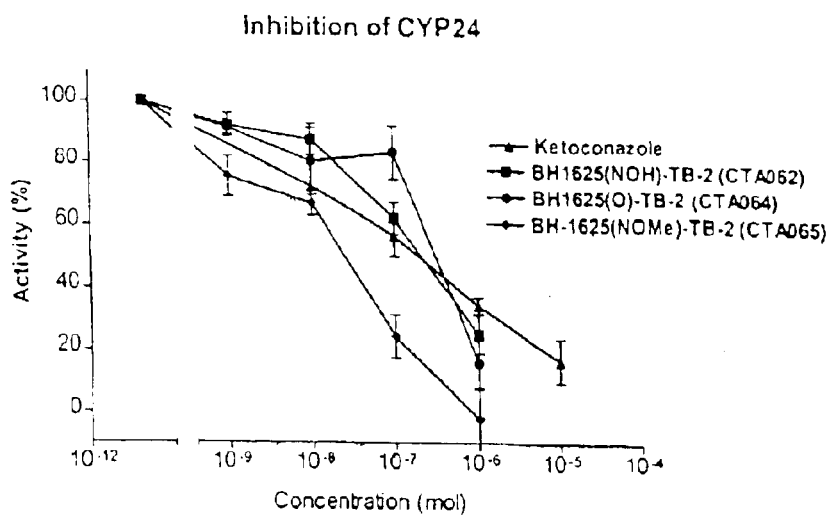
FIG. 1A is a graph showing the inhibition of CYP24 activity by compounds I(a) and I(c) (indicated as BH1625 (NOH)-TB-2 (CTA062) and BH-1625(NOMe)-TB-2-(CTA065) respectively) compared to ketoconazole.

The term "$C_{1-6}$alkyl" as used herein means straight and/or branched chain, saturated or unsaturated alkyl radicals containing from one to six carbon atoms and includes methyl, ethyl, propyl, isopropyl, s-butyl, t-butyl, neopentyl, vinyl, allyl, butenyl and the like.

The term "$C_{1-6}$alkoxy" as used herein means straight and/or branched chain, saturated or unsaturated alkoxy radicals containing from one to six carbon atoms and includes methoxy, ethoxy, propyoxyl, isopropyloxy, t-butoxy and the like.

The term "cyclo($C_3$–$C_6$)alkyl" as used herein means saturated or unsaturated, non-aromatic cyclic alkyl radicals containing from three to six carbon atoms and includes cyclopropyl, cyclopentyl, cyclohexyl, cyclopentenyl, cyclohexenyl and the like.

The term "$C_{1-4}$alkyl" as used herein means straight and/or branched chain, saturated or unsaturated, alkyl radicals containing from one to four carbon atoms and includes methyl, ethyl, propyl, isopropyl, s-butyl, t-butyl and the like.

The term "$C_{1-4}$alkoxy" as used herein means straight and/or branched chain, saturated or unsaturated alkoxy radicals containing from one to four carbon atoms and includes methoxy, ethoxy, propyoxyl, isopropyloxy, t-butoxy and the like.

The term "aryl" as used herein means unsubstituted or substituted mono- or bicyclic aromatic radicals containing from 6 to 10 carbon atoms and includes phenyl and naphthyl and the like.

The term "heteroaryl" as used herein means unsubstituted or substituted mono- or bicyclic heteroaromatic radicals containing from 5 to 10 atoms, of which 1–3 atoms may be a heteroatom selected from the group consisting of S, O and N, and includes furanyl, thienyl, pyrrolo, pyridyl, indolo, benzofuranyl and the like.

The term "aryl-$C_{1-6}$alkyl" as used herein means unsubstituted or substituted mono- or bicyclic aromatic radicals containing from 6 to 10 carbon atoms attached to the compounds of the invention via branched or unbranched alkylene radicals contain from 1–6 carbons atoms, the alkylene radicals being, saturated or unsaturated and unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}alkyl)(C_{1-4}alkyl)$, and includes Ph—C($CH_3$)$_2$—, naphtylmethyl, benzyl and the like.

The term "heteroaryl-$C_{1-6}$alkyl" as used herein means unsubstituted or substituted mono- or bicyclic heteroaromatic radicals containing from 5 to 10 atoms, of which 1–3 atoms may be a heteroatom selected from the group consisting of S, O and N attached to the compounds of the invention via branched or unbranched alkylene radicals contain from 1–6 carbons atoms, the alkylene radicals being saturated or unsaturated and unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}alkyl)(C_{1-4}alkyl)$, and includes thienyl-$CH_2$—, pyridyl-$CH_2$—, indolo-$CH_2$- and the like.

The term "halo" as used herein means halogen and includes chloro, flouro, bromo, iodo and the like.

The term "solvate" as used herein means a compound of the invention, or a salt of a compound of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formulae I and II, and salts, hydrates, solvates and prodrugs thereof.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compound of the invention, or any of its intermediates. Basic compounds of the invention that may form an acid addition salt include, for example, those where aryl, heteroaryl and/or the $C_{1-6}$alkyl group of $R^4$ and/or $R^5$ is substituted with a group having a basic nitrogen, for example $NH_2$ and $NHC_{1-4}$alkyl. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g. oxalates, may be used, for example, in the isolation of the compounds of the invention, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the invention, or any of its intermediates. Acidic compounds of the invention that may form a basic addition salt include, for example, those where aryl and/or heteroaryl is substituted with a group having acidic hydrogen, for example C(O)OH. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the invention, for laboratory use, or for subsequent conversion to a pharmaceutically acceptable acid addition salt.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that modulates CYP24 activity, an effective amount of an agent is, for example, an amount sufficient to achieve such a modulation in CYP24 activity as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as CYP24 activity) as well as the enhancement of a function or activity.

To "inhibit" or "suppress" or "reduce" a function or activity, such as CYP24 activity, is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

The term "cancer cells" as used herein includes all forms of cancer or neoplastic disease.

The term "catabolism" as used herein refers to the metabolic process by which organisms convert substances into compounds for excretion.

The term "1α,3β-stereochemistry" as used herein refers to the relative configuration of the groups, $R^1$ and $R^2$, in which $R^2$ is above the plane of the page, and the $R^1$ is below the plane of the page. The term "1β,3α-stereochemistry" as used herein refers to the relative configuration of the groups, $R^1$ and $R^2$, in which $R^1$ is above the plane of the page, and the $R^2$ is below the plane of the page.

II. Compounds of the Invention

Novel compounds showing selective inhibition of the enzyme CYP24, antiproliferative activity and that are low-calcemic have been prepared. As such, the compounds of the invention are useful for treating cell proliferative diseases, such as cancer.

Accordingly, the present invention provides compounds of Formula I, and pharmaceutically acceptable salts, hydrates, solvates, and prodrugs thereof:

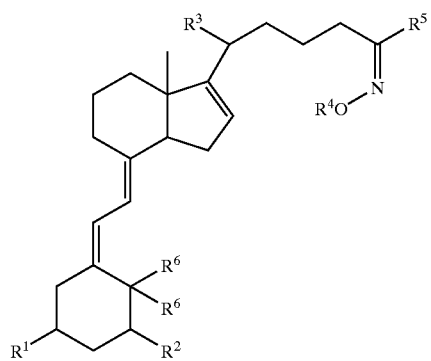

I wherein
$R^1$ and $R^2$ are independently selected from the group consisting of OH, $OC_{1-6}$alkyl, and halo;
$R^3$ is $C_{1-6}$alkyl;
$R^4$ is selected from the group consisting of H, $C_{1-6}$alkyl, aryl and heteroaryl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with aryl and heteroaryl being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$;
$R^5$ is selected from the group consisting of $C_{1-6}$alkyl, cyclo($C_3$–$C_6$)alkyl, aryl, heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with cyclo($C_3$–$C_6$)alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$; and
$R^6$ are either both H or together form $=CH_2$.

The compounds of Formula I include those in which $R^1$ and $R^2$ are independently selected from the group consisting of OH, $OC_{1-6}$alkyl, and halo. In embodiments of the invention, $R^1$ and $R^2$ are independently selected from the group consisting of OH, $OCH_3$, and fluoro. In a further embodiment; $R^1$ and $R^2$ are both OH.

The present invention also includes compounds of Formula I wherein $R^3$ is $C_{1-6}$alkyl. In an embodiment of the invention, $R^3$ is $C_{1-4}$alkyl. In further embodiments, $R^3$ is $CH_3$.

The present invention includes compounds of Formula I wherein $R^4$ is selected from the group consisting of H, $C_{1-6}$alkyl, aryl and heteroaryl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with aryl and heteroaryl being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. In embodiments of the invention, $R^4$ is selected from the group consisting of H, $C_{1-4}$alkyl, and phenyl, with $C_{1-4}$alkyl being unsubstituted or substituted with 1–2 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with phenyl being unsubstituted or substituted with 1–3 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. In further embodiments, $R^4$ is selected from the group consisting of H, phenyl and $C_{1-4}$alkyl. In still further embodiments, $R^4$ is selected from the group consisting of H, phenyl, allyl and $CH_3$.

The present invention includes compounds of Formula I wherein $R^5$ is selected from the group consisting of $C_{1-6}$alkyl, cyclo($C_3$–$C_6$)alkyl, aryl and heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with cyclo($C_3$–$C_6$) alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. In embodiments of the invention, $R^5$ is selected from the group consisting of $C_{1-4}$alkyl, phenyl, and phenyl-$C_{1-6}$alkyl with $C_{1-4}$alkyl being unsubstituted or substituted with 1–2 groups independently selected from $C_{1-4}$alkyl, $OC_{1-4}$alkyl, OH, halo, $NH_2$, $NHC_{1-4}$alkyl and $N(C_{1-4}$alkyl$)(C_{1-4}$alkyl$)$, and with phenyl and phenyl-$C_{1-6}$alkyl being unsubstituted or substituted with 1–3 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. In further embodiments, $R^5$ is selected from the group consisting of $C_{1-4}$alkyl, phenyl, and phenyl-$C_{1-4}$alkyl with $C_{1-4}$alkyl being unsubstituted or substituted with 1–2 groups independently selected from $C_{1-2}$alkyl, $OC_{1-2}$alkyl, OH, halo, $NH_2$, $NHC_{1-2}$alkyl and $N(C_{1-2}$alkyl$)(C_{1-2}$alkyl$)$, and with phenyl and phenyl-$C_{1-4}$alkyl being unsubstituted or substituted with 1–3 groups independently selected from $C_{1-4}$alkyl, $OC_{1-4}$alkyl, OH, $CF_3$, $OCF_3$, halo, $NH_2$, $NHC_{1-4}$alkyl, $N(C_{1-4}$alkyl$)(C_{1-4}$alkyl$)$, and CN. In still further embodiments, $R^5$ is selected from isopropyl, s-butyl, t-butyl, neopentyl.

The present invention also includes compounds of Formula I, wherein $R^6$ are either both H or together form $=CH_2$. In embodiments of the invention, $R^6$ are both H.

All of the compounds of Formula I have more than one asymmetric centre. Where the compounds according to the invention possess more than one asymmetric centre, they may exist as diastereomers. It is to be understood that all such isomers and mixtures thereof in any proportion are encompassed within the scope of the present invention. Further, the invention extends to all geometric isomers of the present invention. For example, where there is a double bond in a compound of the invention, there may exist geometric isomers, such as cis and trans (also known as Z and E) isomers. The stereochemistry of the compounds of the invention is preferably that of natural $1\alpha,25$-dihydroxy vitamin $D_3$. Therefore, in a preferred embodiment, the present invention provides compounds of Formula I with the relative stereochemistry as shown below, and pharmaceutically acceptable salts, hydrates, solvates and prodrugs thereof

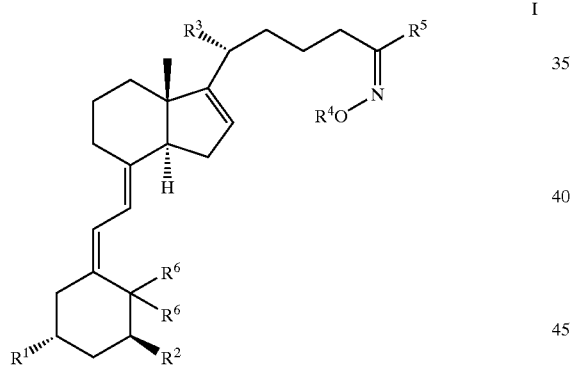

I wherein $R^1$–$R^6$ are as previously defined. It is to be understood that while, the relative stereochemistry of the compounds of Formula I is preferably as shown above, such compounds of Formula I may also contain certain amounts (e.g. less than 20%, preferably less than 10%, more preferably less than 5%) of compounds of Formula I having alternate stereochemistry. For example, a compound of Formula I having the $1\alpha,3\beta$-stereochemistry of natural $1\alpha,25$-Dihydorxy Vitamin $D_3$, shown above, may contain less then 20%, preferably less then 10%, more preferably less then 5%, of a compound of Formula I having the unnatural $1\beta,3\alpha$-sterochemistry.

In specific embodiments of the present invention, the compounds of the invention include:

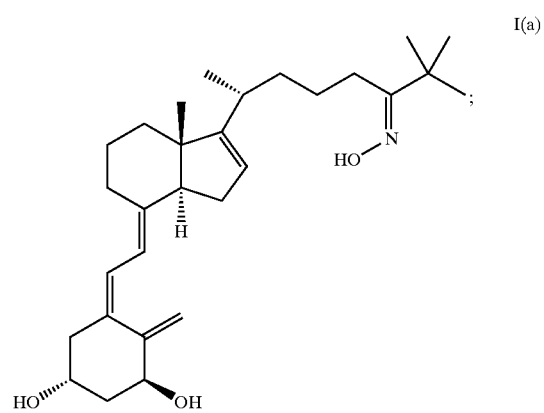

I(a)

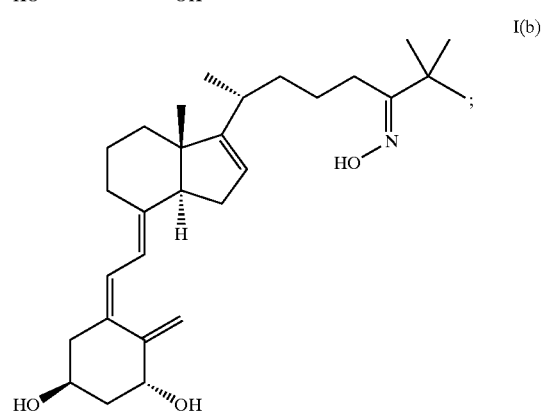

I(b)

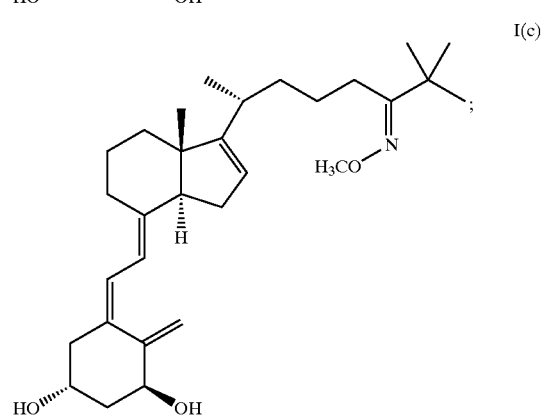

I(c)

-continued
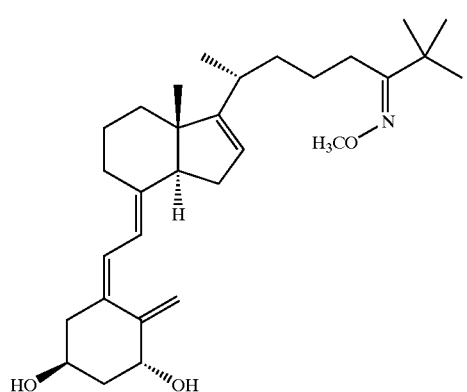
I(d)
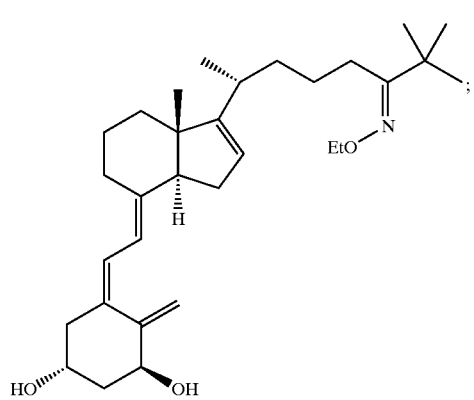
I(e)
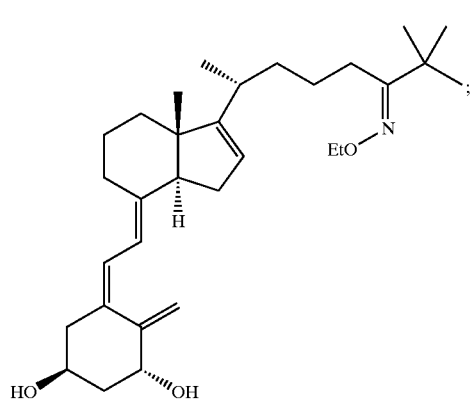
I(f)
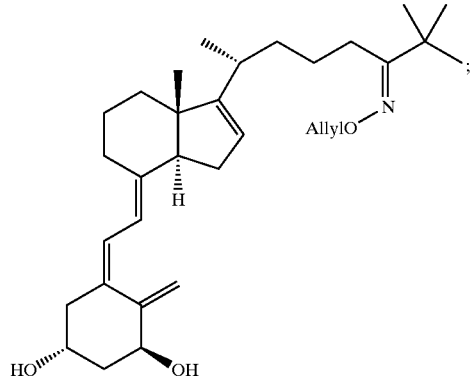
I(g)
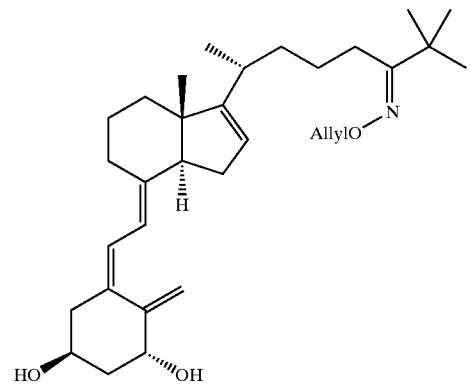
I(h)
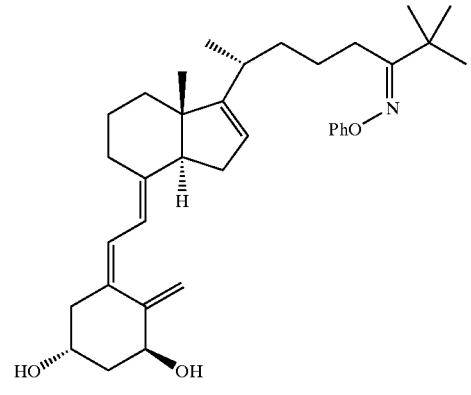
I(i)
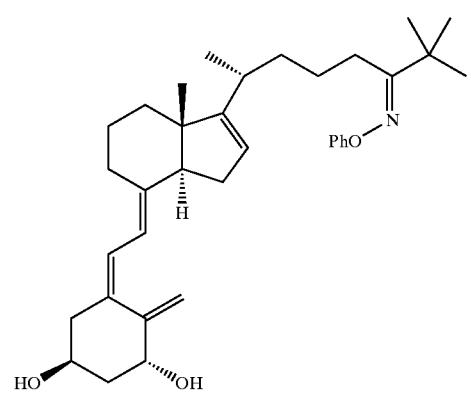
I(j)
and
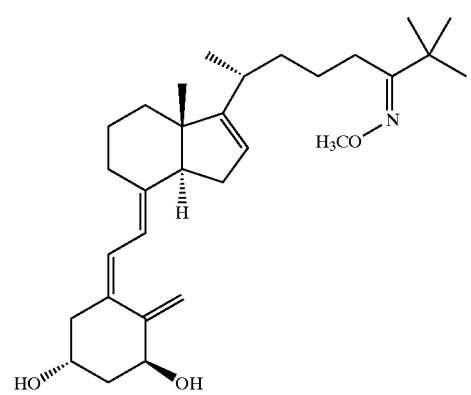
I(k)

and pharmaceutically acceptable salts, hydrates, solvates and prodrugs thereof. Preferred compounds of the invention include compounds I(a), I(c), I(e), I(g), I(i) and I(k) as shown above, and pharmaceutically acceptable salts, hydrates, solvates and prodrugs thereof.

The present invention further provides novel compounds useful in the preparation of the compounds of Formula I. Therefore the present invention further provides compounds of Formula II, and salts, hydrates and solvates thereof:

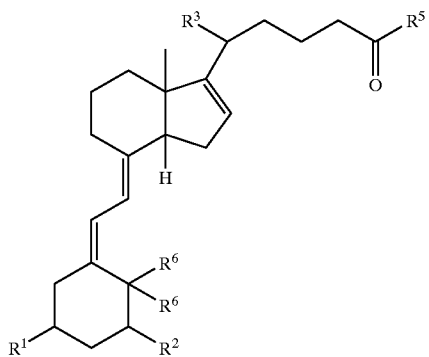

II wherein
$R^1$ and $R^2$ are independently selected from the group consisting of OH, $OC_{1-6}$alkyl, OPG and halo;
PG is a protecting group;
$R^3$ is $C_{1-6}$alkyl;
$R^5$ is selected from the group consisting of $C_{1-6}$alkyl, cyclo($C_3$–$C_6$)alkyl, aryl and heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with cyclo($C_3$–$C_6$)alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)O$C_{1-4}$alkyl, C(O)NH$C_{1-4}$alkyl, NHC(O)$C_{1-4}$alkyl, OC(O)$C_{1-4}$alkyl, SO$C_{1-4}$alkyl, SO$_2C_{1-4}$alkyl, SO$_2$NH$C_{1-4}$alkyl and SO$_2$NH$_2$; and
$R^6$ are either both H or together form =$CH_2$.

The compounds of Formula II include those in which $R^1$ and $R^2$ are independently selected from the group consisting of OH, $OC_{1-6}$alkyl, OPG and halo. In embodiments of the invention, $R^1$ and $R^2$ are independently selected from the group consisting of OH, $OCH_3$, OPG and fluoro. In a further embodiment, $R^1$ and $R^2$ are both OH or OPG. Further, PG is meant to include any protecting group that protects the free OH groups of $R^1$ and/or $R^2$ in the compounds of Formula I from unwanted side reactions during the conversion of compounds of Formula II to compounds of Formula I, and that can be removed under conditions that do not cause unwanted side reactions with other functional groups on the molecule. Suitable protecting groups include trialkylsilyl groups, such as t-butyldimethylsilyl.

The present invention further includes compounds of Formula II wherein $R^3$ is $C_{1-6}$alkyl. In embodiments of the invention, $R^3$ is $C_{1-4}$alkyl. In further embodiments, $R^3$ is $CH_3$.

The present invention also includes compounds of Formula II wherein $R^5$ is selected from the group consisting of $C_{1-6}$alkyl, cyclo($C_3$–$C_6$)alkyl, aryl and heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with cyclo($C_3$–$C_6$)alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)O$C_{1-4}$alkyl, C(O)NH$C_{1-4}$alkyl, NHC(O)$C_{1-4}$alkyl, OC(O)$C_{1-4}$alkyl, SO$C_{1-4}$alkyl, SO$_2C_{1-4}$alkyl, SO$_2$NH$C_{1-4}$alkyl and SO$_2$NH$_2$. In embodiments of the invention, $R^5$ is selected from the group consisting of $C_{1-4}$alkyl, phenyl, and phenyl-$C_{1-6}$alkyl with $C_{1-4}$alkyl being unsubstituted or substituted with 1–2 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with phenyl and phenyl-$C_{1-6}$alkyl being unsubstituted or substituted with 1–3 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)O$C_{1-4}$alkyl, C(O)NH$C_{1-4}$alkyl, NHC(O)$C_{1-4}$alkyl, OC(O)$C_{1-4}$alkyl, SO$C_{1-4}$alkyl, SO$_2C_{1-4}$alkyl, SO$_2$NH$C_{1-4}$alkyl and SO$_2$NH$_2$. In further embodiments, $R^5$ is selected from the group consisting of $C_{1-4}$alkyl, phenyl, and phenyl-$C_{1-4}$alkyl with $C_{1-4}$alkyl being unsubstituted or substituted with 1–2 groups independently selected from $C_{1-2}$alkyl, $OC_{1-2}$alkyl, OH, halo, $NH_2$, $NHC_{1-2}$alkyl and $N(C_{1-2}$alkyl)($C_{1-2}$alkyl), and with phenyl and phenyl-$C_{1-4}$alkyl being unsubstituted or substituted with 1–3 groups independently selected from $C_{1-4}$alkyl, $OC_{1-4}$alkyl, OH, $CF_3$, $OCF_3$, halo, $NH_2$, $NHC_{1-4}$alkyl, $N(C_{1-4}$alkyl)($C_{1-4}$alkyl), and CN. In still further embodiments, $R^5$ is selected from isopropyl, s-butyl, t-butyl, neopentyl.

The present invention also includes compounds of Formula I, wherein $R^6$ are either both H or together form =$CH_2$. In embodiments of the invention, $R^6$ are both H.

In specific embodiments of the present invention, the compounds of the Formula II include:

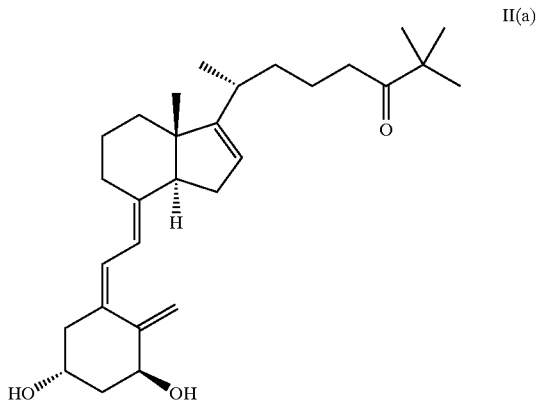

II(a)

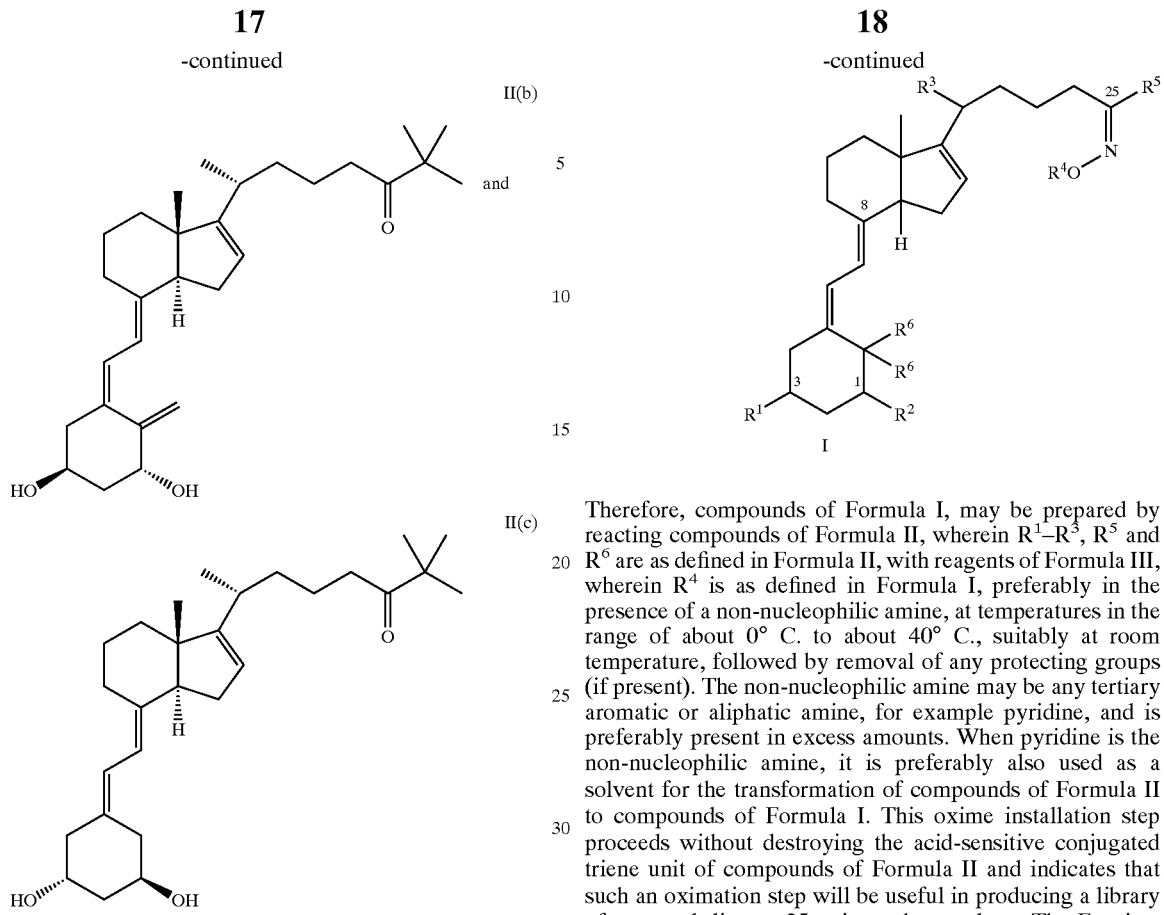

II(b)

and

II(c)

and salts, hydrates and solvates thereof. Preferred compounds of Formula II are compounds II(a) and II(c), as shown above, and salts, hydrates and solvates thereof.

III. Methods of Preparing Compounds of the Invention

In accordance with another aspect of the present invention, the compounds of the invention can be prepared by processes analogous to those established in the art. Therefore, compounds of this invention may be prepared, for example, by the reaction sequence shown in Scheme 1:

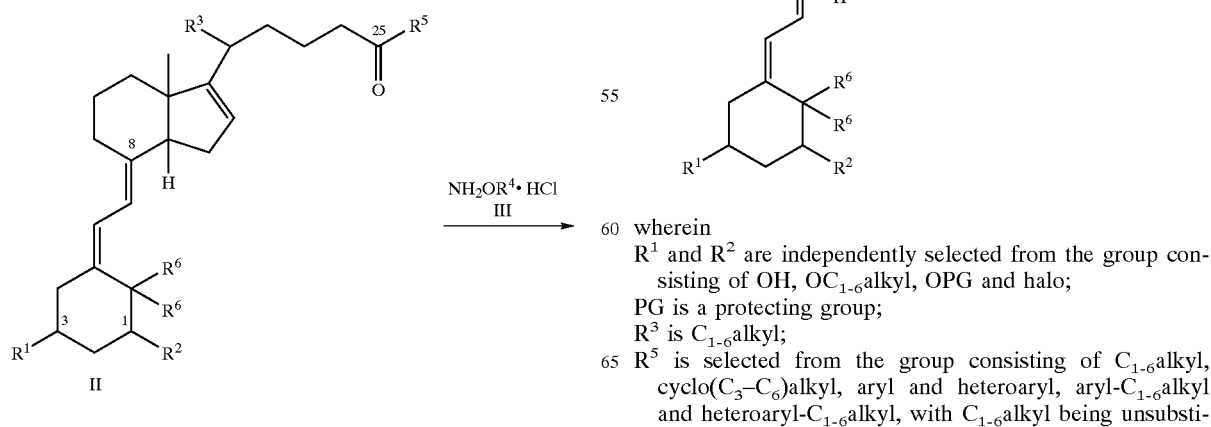

Therefore, compounds of Formula I, may be prepared by reacting compounds of Formula II, wherein $R^1$–$R^3$, $R^5$ and $R^6$ are as defined in Formula II, with reagents of Formula III, wherein $R^4$ is as defined in Formula I, preferably in the presence of a non-nucleophilic amine, at temperatures in the range of about 0° C. to about 40° C., suitably at room temperature, followed by removal of any protecting groups (if present). The non-nucleophilic amine may be any tertiary aromatic or aliphatic amine, for example pyridine, and is preferably present in excess amounts. When pyridine is the non-nucleophilic amine, it is preferably also used as a solvent for the transformation of compounds of Formula II to compounds of Formula I. This oxime installation step proceeds without destroying the acid-sensitive conjugated triene unit of compounds of Formula II and indicates that such an oximation step will be useful in producing a library of new and diverse 25-oxime ether analogs. The E-oxime alkyl ether of the Formula I is predominately obtained due to the strongly unfavourable steric congestion that would be present in the corresponding Z-oxime alkyl ether (see Hawkes, G. E. and Herwig, K.; Roberts, J. D. *J. Org. Chem.* 1974, 39, 1017–1028).

Accordingly, the present invention provides a method for preparing a compound of Formula I comprising reacting a compound of Formula II, or a salt, hydrate or solvate thereof:

wherein
$R^1$ and $R^2$ are independently selected from the group consisting of OH, $OC_{1-6}$alkyl, OPG and halo;
PG is a protecting group;
$R^3$ is $C_{1-6}$alkyl;
$R^5$ is selected from the group consisting of $C_{1-6}$alkyl, cyclo($C_3$–$C_6$)alkyl, aryl and heteroaryl, aryl-$C_{1-6}$alkyl and heteroaryl-$C_{1-6}$alkyl, with $C_{1-6}$alkyl being unsubstituted or substituted with 1–4 groups independently selected from C$_{1-4}$alkyl, OC$_{1-4}$alkyl, OH, halo, NH$_2$, NHC$_{1-4}$alkyl and N(C$_{1-4}$alkyl)(C$_{1-4}$alkyl), and with cyclo (C$_3$–C$_6$)alkyl, aryl, heteroaryl, aryl-C$_{1-6}$alkyl and heteroaryl-C$_{1-6}$alkyl, being unsubstituted or substituted with 1–5 groups independently selected from C$_{1-4}$alkyl, OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$; and R$^6$ are either both H or together form =CH$_2$, with a compound of Formula III, or a salt hydrate of solvate thereof:

III, wherein R$^4$ is selected from the group consisting of H, C$_{1-6}$alkyl, aryl and heteroaryl, with C$_{1-6}$alkyl being unsubstituted or substituted with 1–4 groups independently selected from C$_{1-4}$alkyl, OC$_{1-4}$alkyl, OH, halo, NH$_2$, NHC$_{1-4}$alkyl and N(C$_{1-4}$alkyl)(C$_{1-4}$alkyl), and with aryl and heteroaryl being unsubstituted or substituted with 1–5groups independently selected from C$_{1-4}$alkyl-OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$;

in the presence of non-nucleophilic amine, followed by removal of any protecting groups, if present.

Ketones of Formula II, wherein R$^1$–R$^3$, R$^5$ and R$^6$ are as defined in Formula I, may be prepared, for example, as shown in Scheme 2:

Scheme 2

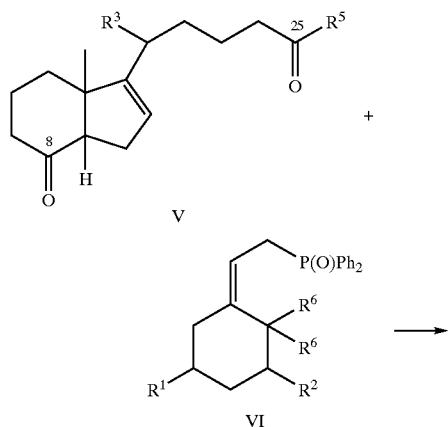

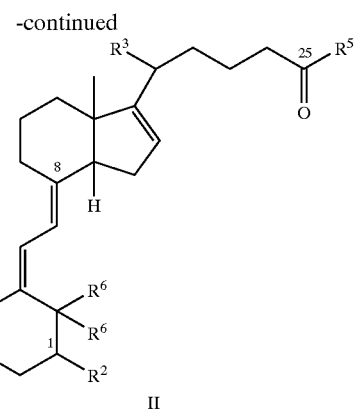

II

Ketones of Formula V, wherein R$^3$ and R$^5$ are as defined in Formula I, may be chemospecifically mono-olefinated at C-8 (due to steric hindrance at C-25) with phosphine oxides of Formula VI, wherein R$^1$, R$^2$ and R$^6$ are as defined in Formula I, under standard Horner-Wadsworth-Emmons (HWE) coupling conditions (see Posner, G. H. et al. *J. Org. Chem.* 1997, 62, 3299–3314). Therefore phosphine oxides VI are treated with a strong base, for example an alkyl lithium such as phenyl lithium, under anhydrous conditions in an inert atmosphere and solvent, for example tetrahydrofuran (THF), at temperatures in the range of about –60° C. to about –90° C., suitably at about –78° C. To the resulting intermediate ylide is added a cold, preferably at about –78° C., solution of a ketone V in an inert solvent such as THF while maintaining the anhydrous conditions. After removal of any protecting groups using standard chemistries (if needed), compounds of Formula II may be obtained.

Ketones of Formula V, wherein R$^3$ and R$^5$ are as defined in Formula I, may be prepared, for example, as shown in Scheme 3:

Scheme 3

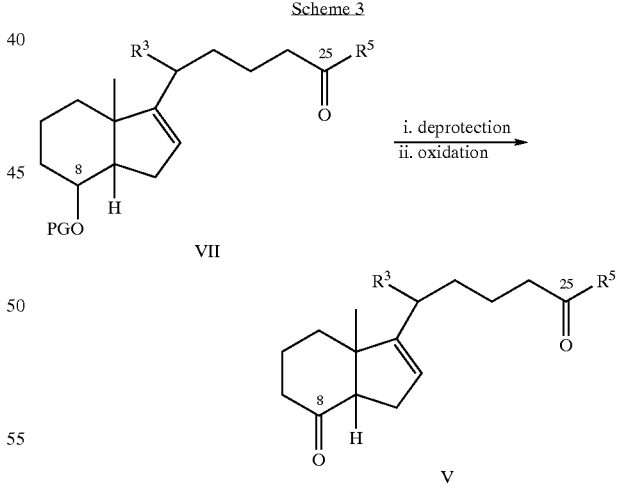

Suitably protected compounds of the Formula VII, wherein R$^3$ and R$^5$ are as defined in Formula I and PG is a suitable protecting group, are first deprotected and then oxidized to provide ketones V. For example, when PG is trialkyl silyl, such as triethyl silyl, deprotection may be affected by reacting compounds of Formula VII with tetrabutylammonium fluoride (TBAF) in an inert solvent, such as THF, and in an inert atmosphere, suitably at about room temperature. Oxidation of the resulting alcohol may be performed, for example, using 4-methylmorpholine-N-oxide (NMO), or any other suitable oxidizing agent, in an inert solvent such as methylene chloride, under standard conditions.

Compounds of Formula VII, wherein $R^3$ and $R^5$ are as defined in Formula I and PG is a suitable protecting group, may be obtained, for example, as shown in Scheme 4:

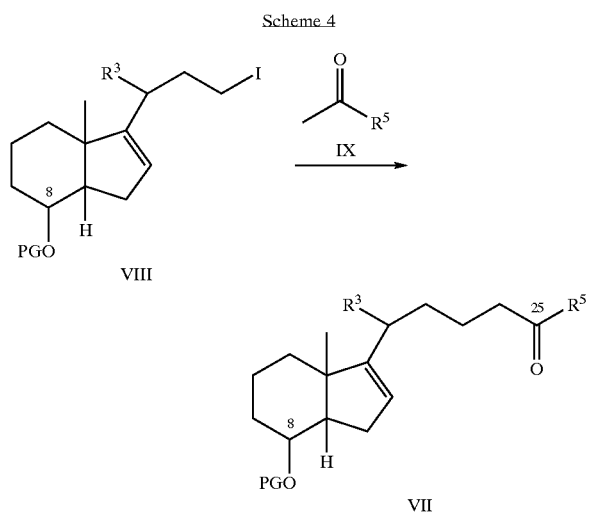

Compounds of Formula VIII, wherein $R^3$ is as defined in Formula I and PG is a suitable protecting group, may be reacted with the anion of compounds of Formula IX, wherein $R^5$ is as defined in Formula I under anhydrous conditions at temperatures in the range of about −60° C. to about −90° C., suitably at about −78° C. The anions of compounds of Formula IX may be prepared by treating compounds of Formula IX with a strong base, for example an alkyl lithium such as n-butyl lithium or lithium diisopropylamide (LDA), under inert conditions and, in the presence of hexamethyl phosphoramide (HMPA), for example, or $N_1$, N, $N^1$, $N^1$-tetramethy ethylenediamine (TMEDA).

Compounds of Formula IX, wherein $R^5$ is as defined in Formula I are either commercially available or may be prepared, for example, by the oxidation of the corresponding alcohols as shown in Scheme 5:

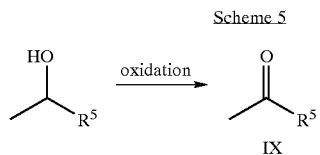

Examples of oxidizing agents include pyridium dichromate (PDC), m-chloroperbenzoic acid (mCPBA) and manganese dioxide.

The preparation of compounds of Formula VIII, wherein $R^3$ is as defined in Formula I and PG is a suitable protecting group, is known in the art. Therefore compounds of Formula VIII may be prepared as described in Posner, G. H. et al. *J. Med. Chem.* 1999, 42, 3425–3435.

The preparation of compounds of Formula VI, wherein $R^1$, $R^2$ and $R^6$ are as defined in Formula I is known in the art. Therefore compounds of Formula VI may be prepared as described in Posner, G. H. et al. *J. Med. Chem.* 1992, 35, 3280–3287, the contents of which are incorporated herein by reference.

The preparation of enantiomerically pure compounds of Formula I and or II, may be accomplished by using enantiomerically pure compounds of Formula V and VI in the reaction shown in Scheme 2. In this reaction, a mixture of the 1α,3β and 1β, 3α diasteromers is typically obtained, with the 1α,3β diastereomer as the major product. These diasteromers may be separated using chromatography, for example using high performance liquid chromatography (HPLC).

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of Formula I may be, for example, conventional esters formed with available hydroxy, thiol, amino or carboxyl group. For example, when $R^1$ and/or $R^2$ is OH it may be acylated using an activated acid in the presence of a base, and optionally, in inert solvent (e.g. an acid chloride in pyridine). Some common esters which have been utilized as prodrugs are phenyl esters, aliphatic ($C_8$–$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50–100° C.

IV. Uses

As hereinbefore mentioned, novel compounds of the Formulae I and II have been prepared. Accordingly, the present invention includes all uses of the compounds of the invention including their use in therapeutic methods and compositions for modulating cell proliferation, their use in diagnostic assays and their use as research tools and as starting materials and/or intermediates in the preparation of other chemical entities.

Inhibiting catabolism of calcitriol will lengthen the biological lifetime of this hormone and thus allow smaller amounts of it to be used for effective human chemotherapy; such smaller dosing will avoid, or at least minimize, the hypercalcemic toxicity associated with medicinal use of calcitriol. Selectively inhibiting the cytochrome P450 enzymatic pathway, through which calcitriol is catabolized (mainly via C-24 hydroxylation), is one important way to prolong the lifetime of this hormone. Therefore, the compounds of Formula I were tested in vitro, using a standard protocol, for their ability to inhibit specifically CYP24, responsible for 24-hydroxylation of calcitriol. Antimycotic ketoconazole, a drug used clinically for chemotherapy of human prostate cancer (Trachtenberg, J. et al. J. Urol. 1984, J32, 61–63), was used as a control standard for inhibition of CYP24. Selected compounds of Formula I were more potent than ketoconazole in inhibiting CYP24 activity. These compounds showed little to no inhibition of the enzymes CY627A1 and CYP27B 1, indicating that the can selectively inhibit CYP24 activity.

Selected compounds of Formula I have also been shown to have in vitro antiproliferative activity in murine keratinocytes. Also, in standard hypercalcemia assays, selected compounds of Formula I did not increase the levels of calcium in the urine of a rat after they were administered orally to the rats daily for one week. At similar doses, calcitriol causes a significant increase in calcium levels in the urine.

The compounds of Formula I are CYP24 modulators and are useful in modulating CYP24 activity, including the inhibition of CYP24 activity, for the treatment of various conditions such as cell proliferative disorders. Accordingly, the invention provides a method of modulating CYP24 activity by administering an effective amount of a compound of Formula I to a cell or animal in need thereof. In a further aspect, the invention provides a method of inhibiting CYP24 activity by administering an effective amount of a compound of Formula I to a cell or animal in need thereof. The present invention also includes the use of a compound of Formula I to modulate, preferably to inhibit, CYP24 activity and a use of a compound of Formula I to prepare a medicament to modulate, preferably to inhibit, CYP24 activity.

By selectively modulating CYP24, the enzyme that metabolizes $1\alpha,25$-dihydroxy vitamin $D_3$, the levels of $1\alpha,25$-dihydroxy vitamin $D_3$ will be modulated. Diseases that benefit from a modulation of the levels of $1\alpha,25$-dihydroxy vitamin $D_3$ can therefore be treated using a modulator of CYP24. By acting preferentially on CYP24, side effects caused by interaction with other enzymes and receptors will be reduced. Accordingly, the present invention provides a method for treating diseases which benefit from a modulation of the levels of $1\alpha,25$-dihydroxy vitamin $D_3$ comprising administering an effective amount of a compound of Formula I to, a cell or animal in need thereof. The invention also includes the use of a compound of Formula I to modulate the levels of $1\alpha,25$-dihydroxy vitamin $D_3$. Further, the invention includes a use of a compound of Formula I to prepare a medicament to modulate the levels of $1\alpha,25$-dihydroxy vitamin $D_3$.

Inhibition of CYP24, will inhibit the catabolism $1\alpha,25$-dihydroxy vitamin $D_3$ which will lengthen the biological lifetime of this hormone and allow smaller amounts of it to be used for effective disease treatment. Such smaller dosing will avoid, or at least minimize, the hypercalcemic toxicity associated with medicinal use of $1\alpha,25$-dihydroxy vitamin $D_3$ (calcitriol). Therefore, in an embodiment, the present invention provides a method for treating diseases which benefit from inhibiting the catabolism of $1\alpha,25$-dihydroxy vitamin $D_3$ comprising administering an effective amount of a compound of Formula I to a cell or animal in need thereof. The invention also includes the use of a compound of Formula I to inhibit the catabolism of $1\alpha:25$-dihydroxy vitamin $D_3$. Further, the invention includes a use of a compound of Formula I to prepare a medicament to inhibit the metabolism of $1\alpha,25$-dihydroxy vitamin $D_3$.

Diseases which may benefit for a modulation in the levels of $1\alpha,25$-dihydroxy vitamin $D_3$ include, but are not limited to:

(i) in the parathyroid—hyper- and hypo-parathyroidism, Pseudohypoparathyroidism, Secondary hyperparathyroidism;
(ii) in the pancreas—diabetes;
(iii) in the thyroid—medullary carcinoma;
(iv) in the skin—psoriasis, wound healing;
(v) in the lung—sarcoidosis and tuberculosis;
(vi) in the kidney—chronic renal disease, hypophosphatemic VDRR, vitamin D dependent rickets;
(vii) in the bone—anticonvulsant treatment, fibrogenisis imperfecta ossium,osteitits fibrosa cystica, osteomalacia, osteoporosis, osteopenia, osteosclerosis, renal osteodytrophy, rickets;
(viii) in the intestine—glucocorticoid antagonism, idopathic hypercalcemia, malabsorption syndrome, steatorrhea, tropical sprue.

In one aspect, the present invention provides a method for modulating cell proliferation comprising administering an effective amount of a compound of Formula I to a cell or animal in need thereof. Preferably, the invention provides a method of inhibiting cell proliferation comprising administering an effective amount of a compound of Formula I to a cell or animal in need thereof. The present invention also includes a use of a compound of Formula I in order to modulate, preferably to inhibit, cell proliferation. The present invention further includes a use of a compound of Formula I to prepare a medicament to modulate, preferably to inhibit, cell proliferation. In particular, the method of the invention is useful in inhibiting the proliferation of abnormal but not normal cells. Abnormal cells include any type of cell that is causative of or involved in a disease or condition and wherein it is desirable to modulate or inhibit the proliferation of the abnormal cell to treat the disease or condition. Examples of abnormal cells include malignant or cancerous cells as well as cell that over-proliferate in inflammatory conditions such as psoriasis. In an embodiment of the invention, the cell proliferative disorder is cancer, in particular cancer of the breast, prostate and lung.

While the compounds of the invention may act by modulating CYP24 activity, one of skill in the art will appreciate that other modes or mechanisms of action for the compounds of Formula I are possible.

One skilled in the art can determine which compounds of Formula I would have therapeutic utility, for example, in inhibiting cell proliferation in any type of cancer or cell proliferative disorder. Compounds may be examined for their efficacy in inhibiting cell growth in cell proliferation assays such as inhibition of growth of murine keratinocyte cells (cell line PE) as described in Example 13 herein, and for the inhibition of TPA-induced ornithine decarboxylase (ODC) activity as described in U.S. Pat. No. 5,830,885, the contents of which are incorporated herein by reference. The compounds of Formula I may also be screened for their propensity to cause hypercalcemia using the method described in Example 14 herein. Compounds showing hypercalcemia are not desirable.

In addition to cancer, the compounds of Formula I are useful in treating other conditions involving aberrant or abnormal cell proliferation. Other cell proliferative disorders that may be treated by the present invention include inflammatory diseases, allergies, autoimmune disease, graft rejection, psoriasis, restenosis, artherosclerosis, and any other disorder wherein it is desirable to inhibit, prevent or suppress cell growth. Compounds of Formula I may be tested for their efficacy in a particular cell proliferation disorder using assays and techniques known to those of skill in the art. For example, the following references provide assays for various conditions: Rheumatoid Arthritis: "Regulation of IL-15—Simulated TNF-alpha Production by Rolipram", Journal of Immunology (1999) volume 163 page 8236 by C. S. Kasyapa et al.; Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al.; Psoriasis: Journal of Immunology (2000) volume 165 page 224 "Inhibition of Keratinocyte apoptosis by IL-15: a new parameter in the pathegenosis of psoriasis" by R. Üchert; and Psoriasis: International Archives of allergy and Immunology (2000) Volume 123 page 275. "T-cell receptor mimic peptides and their potential application in T-cell mediated disease" by A. H. Enk.

The compounds of Formula I are preferably formulated into pharmaceutical compositions for administration to human subjects in a biologically compatible form suitable for administration in vivo. Accordingly, in another aspect, the present invention provides a pharmaceutical composition comprising a compound of Formula I, or a pharmaceutically acceptable salt, hydrate, solvate or prodrug thereof, in admixture with a suitable diluent or carrier.

The compositions containing the compounds of Formula I can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of Formula I may be used pharmaceutically in the form of the free base, in the form of salts, solvates and as hydrates. All forms are within the scope of the invention. Acid and basic addition salts may be formed with the compounds of the invention (i.e. compounds of Formulae I and II) for use as sources of the free base form even if the particular salt per se is desired only as an intermediate product as, for example, when the salt is formed only for the purposes of purification and identification. All salts that can be formed with the compounds of the invention are therefore within the scope of the present invention.

In accordance with the methods of the invention, the described compounds of Formula I, or salts, solvates, hydrates or prodrugs thereof, may be administered to a patient in a variety of forms depending on the selected route of administration, as will be understood by those skilled in the art. The compounds of Formula I may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of Formula I may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of Formula I may be incorporated with excipient and used in the form of ingestible tablets, buccal tablets, troches, capsules, elixirs, suspensions, syrups, wafers, and the like.

A compound of Formula I may also be administered parenterally. Solutions of a compound of Formula I can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990–18th edition) and in The United States Pharmacopeia: The National Formulary (USP24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of Formula I, or salts, solvates, hydrates or prodrugs thereof, may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds of Formula I and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any and the clearance rate of the compound in the animal to be treated. One of skill in the art can determine the appropriate dosage based on the above factors. The compounds of Formula I may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

The compounds of Formula I, or salts, solvates, hydrates or prodrugs thereof, can be used alone or in combination with other agents that modulate CYP24 activity or in combination with other types of treatment (which may or may not modulate CYP24) for cell proliferative disorders or other disorders that benefit from a modulation in the levels of 1α,25-dihydroxy vitamin $D_3$ and/or an inhibition of the catabolism of 1α,25-dihydroxy vitamin $D_3$. Preferably the compounds of Formula I are administered in combination with 1α,25-dihydroxy vitamin $D_3$ (calcitriol) or other vitamin D receptor agonists. Inhibiting catabolism of vitamin D receptor agonists will lengthen the biological lifetime or efficacy of these therapies and thus to allow smaller amounts of the drug to be used for effective human chemotherapy; such smaller dosing will avoid, or at least minimize, the hypercalcemic toxicity associated with medicinal use of calcitriol or other vitamin D receptor agonists. The present invention therefore provides a method of increasing the efficacy of a vitamin D receptor agonist, preferably 1α,25-dihydroxy vitamin $D_3$ (calcitriol), comprising co-administering an effective amount of a compound of Formula I and an effective amount of the vitamin D receptor agonist, preferably 1α,25-dihydroxy vitamin D3 (calcitriol). Further the invention includes a use of a compound of Formula I to increase the efficacy of a vitamin D receptor agonist, preferably 1α,25-dihydroxy vitamin $D_3$ (calcitriol), and a use of a compound of Formula I to prepare a medicament to increase the efficacy of a vitamin D receptor agonist, preferably 1α,25-dihydroxy vitamin $D_3$ (calcitriol).

In a further aspect of the present invention, the compounds of Formula I, or salts, solvates, hydrates or prodrugs thereof, may be used in combination with other therapies and therapeutics to treat dermatological disorders, bone disorders, thyroid disorders, wound healing and osteoporosis.

In addition to the above-mentioned therapeutic uses, the compounds of the invention are also useful in diagnostic assays, screening assays and as research tools.

In diagnostic assays the compounds of the invention (including compounds of Formula II, which have also been shown to inhibit CYP24, but are calcemic) may be useful in identifying or detecting a cell proliferative disorder. In such an embodiment, the compounds of the invention may be radiolabelled (as hereinbefore described) and contacted with a population of cells. The presence of the radiolabelled on the cells may indicate a cell proliferative disorder.

In screening assays, the compounds of the invention (including compounds of Formula II) may be used to identify other compounds that modulate cell proliferation or CYP24 activity. As research tools, the compounds of the invention may be used in receptor binding assays and assays to study the localization of CYP24. In such assays, the compounds may also be radiolabelled.

The following non-limiting examples are illustrative of the present invention:

EXAMPLES

Materials and Methods

Unless otherwise noted, all reactions were performed in oven-dried glassware stirred under an atmosphere of ultra-high-purity argon. THF was distilled from Na/benzophenone ketyl and $CH_2Cl_2$ distilled from $CaH_2$ immediately prior to use. Organolithiums were titrated prior to use following known methods (Suffert, J. *J. Org. Chem.* 1989, 54, 509–510). Methylene chloride ($CH_2Cl_2$) and thiethylamine ($Et_3N$) were distilled from calcium hydride prior to use. All other reagents were used as received from commercial suppliers. Analytical TLC analysis was conducted on precoated glass-backed silica gel plates (Merck Kieselgel 60 $F_{254}$, 250 mm thickness) and visualized with p-anisaldehyde or $KMnO_4$ stains. Column chromatography was performed using short path silica gel (particle size <230 mesh) or flash silica gel (particle size 230–400 mesh). Preparative-plate chromatography was performed using silica-gel-coated glass preparative plates (500–1000 μm) from Analtech and analyzed by UV. High-performance liquid chromatography (HPLC) was carried out using a Rainin HPLX system equipped with two 25-mL/min preparative pump heads using Rainin Dynamax 10-mm×250-mm (semipreparative) columns packed with 60 Å silica gel (8 μm pore size) as C-18-bonded silica and a Rainin Dynamax UV-C dual-beam variable-wavelength detector set at 265 nm. Yields are reported for pure products (>95% based on their chromatographic and spectroscopic homogeneity) and are unoptimized. Optical rotations were measured at the Na line using a Perkin-Elmer 141 Polarimeter. Nuclear magnetic resonance (NMR) spectra were obtained on a Varian XL-400 spectrometer operating at 400 MHz for $_1H$, and 100 MHz for $^{13}C$. Chemical shifts are reported in ppm (δ) and are referenced to $CDCl_3$ (7.26 ppm for $^1H$ and 77.0 ppm for $^{13}C$), and tetramethylsilane (TMS, 0.00 ppm for $^1H$). Ultraviolet (UV) spectra were obtained using a Cary Bio 400 spectrophotometer at ambient temperature. Infrared specta (IR) spectra were obtained using a Perkin Elmer 1600 Series FT-IR instrument. Absorption bands are reported in wavenumbers ($cm^{-1}$). Low and high resolution mass spectra (LRMS and HRMS) were obtained with electronic of chemical ionization (EI or CI) at the mass spectrometry facility at the Ohio State University on a Micromass QTOF Electrospray mass spectrometer.

Example 1

Preparation of t-Butyl Ketone VII ($R^3=CH_3$, $R^5$=t-Butyl. PG=TES)

A 15 mL round-bottom flask was charged with triisopropylamine (42 mg, 0.41 mmol, 7.4 eq.—distilled over calcium hydride prior to use) and 2 mL distilled THF. This solution was cooled to −78° C., and n-butyllithium (250 μL of 1.6M solution, 0.43 mmol, 7.2 eq.) was added via syringe. Pinacolone (IX, $R^5$=t-Butyl) (39 mg, 0.39 mmol, 7.0 eq.— dried over potassium carbonate and activated molecular sieves for 24 hours immediately prior to use) was dissolved in 1 mL of distilled THF and cooled to −78° C. at which point it was added to the reaction flask via cannula. The reaction was left to stir for 30 minutes. Hexamethylphosphoramide (HMPA, 250 μL) was then added via syringe and the reaction mixture was allowed to stir for an additional 15 minutes. A solution of iodide (−)-VIII($R^3=CH_3$, PG=triethylsilyl (TES)) (25 mg, 0.06 mmol) in 1 mL THF was cooled to −78° C. and added to the reaction mixture via cannula. The reaction mixture was stirred at −78° C. for two hours and then warmed to −41° C. in a dry ice/acetonitrile bath where it was allowed to warm to room temperature over the course of two hours and to stir for an additional 6 hours. The resulting yellow solution was quenched with 2 mL water, extracted with ethyl acetate (3×25 mL), dried over MgSO$_4$, concentrated, and purified using silica gel column chromatography (0–20% ethyl acetate/petroleum ether) to give a colorless oil (18 mg, 76%). $^1$H NMR (400 MHz, CDCl$_3$) δ 5.26 (t, J=1.4 Hz, 1H), 4.11 (d, J=2.0 Hz, 1H), 2.46–1.25 (m, 16H), 1.13 (s, 9H), 1.00 (s, 3H), 0.98–0.96 (d, J=6.8 Hz, 3H), 0.97–0.93 (t, J=8 Hz, 9H), 0.59–0.53 (q, J=7.8 Hz, 6H); $^{13}$C NMR (100 MHz, CDCl$_3$) δ 216.1, 160.2, 119.7, 69.0, 55.1, 46.7, 44.1, 36.6, 36.2, 35.8, 35.0, 31.7, 30.7, 26.4, 22.3, 22.0, 18.7, 18.1, 6.9, 4.9; IR (neat) 2956, 1708, 1607, 1456, 1366, 1235, 1143, 1082, 1029, 972, 725 cm$^{-1}$; $[\alpha]_D$=+19.4; HRMS calcd for C$_{26}$H$_{48}$O$_2$SiNa [M+Na]: 443.3321, found: 443.3318.

Example 2

Preparation of CD-ring Ketone V (R$^3$=CH$_3$, R$^5$=t-Butyl)

A 15 mL round-bottom flask was charged with tert-butyl ketone VII (R$^3$=CH$_3$, R$^5$=t-Butyl, PG=TES) (18 mg, 0.4 mmol) dissolved in 5 mL distilled THF. Tetrabutylammonium fluoride hydrate (TBAF, 112 mg, 10 eq.) and 4 Å molecular sieves (100 mg) were added to the reaction flask and this solution was left to stir at reflux for four hours. Additional portions of TBAF and sieves were added every four hours until starting material was no longer visible by analytical thin layer chromatography (TLC). The reaction solution was filtered through a plug of silica gel using ethyl acetate as the eluent to remove excess TBAF and molecular sieves. This solution was concentrated and a 10 mL round-bottom flask was charged with the resulting material dissolved in 5 mL distilled dichloromethane (CH$_2$Cl$_2$). To this solution was added 4 Å molecular sieves (20 mg), 4-methylmorpholine-N-oxide (NMO, 10 mg, 0.09 mmol, 2 eq.) and a catalytic amount of tetrapropylammonium perruthenate (TPAP). After stirring for 1 hour, TLC showed complete consumption of starting material. The reaction solution was filtered through a plug of silica gel using ethyl acetate as the eluent to remove TPAP and molecular sieves. This solution was concentrated and purified using silica gel column chromatography (20% ethyl acetate/petroleum ether) to give a colorless oil (9 mg, 71%). $^1$H NMR (400 MHz, CDCl$_3$) δ 5.29–5.28 (m, J=1.6 Hz, 1H), 2.87–2.82 (dd, J=10.6, 6.6 Hz, 1H), 2.47–1.31 (m, 16H), 1.12 (s, 9H), 1.05–1.04 (d, J=6.8 Hz, 3H), 0.80 (s, 3H); $^{13}$C NMR (100 MHz, CDCl$_3$) δ 215.9, 211.1, 157.8, 120.3, 63.1, 53.8, 44.1, 40.5, 36.5, 36.0, 34.4, 32.9, 27.1, 26.4, 24.0, 21.9, 21.7, 17.25; IR (neat) 2955, 1702, 1461, 1367 cm$^{-1}$ $[\alpha]_D$=15.6; HRMS calcd for C$_{20}$H$_{32}$O$_2$Na [M+Na]: 327.2300, found: 327.2302.

Example 3

Preparation of II(a) and II(b)

Anhydrous phosphine oxide (±)-VI (R$^1$, R$^2$=O-t-Butyldimethylsilyl (OTBDMS)) (79 mg, 0.14 mmol, 1.4 eq.) was dissolved in 2.5 mL distilled THF and cooled to −78° C. Phenyllithium (88 μL of a 1.7M solution in cyclohexane-ether, 0.15 mmol, 1.5 eq.) was added dropwise via syringe resulting in a deep red color. This solution was left to stir for 20 minutes. Anhydrous CD-ring ketone (+)-V (R$^3$=CH$_3$, R$^5$=t-Butyl) (31 mg, 0.10 mmol) was dissolved in 1.5 mL distilled THF and cooled to −78° C. This solution was then added to the reaction mixture via cannula, and the red color persisted. This solution was stirred at −78° C. in the dark for 7 hours at which point it was quenched with saturated potassium carbonate (1 mL) and potassium sodium tartrate (2 mL of a 2M solution). The product was extracted with ethyl acetate (4×60 mL), dried using MgSO$_4$, filtered, concentrated and purified using silica gel column chromatography (3–10% ethyl acetate/hexanes buffered with 1% Et$_3$N) to give a colorless oil. A 5 mL round-bottom flask was charged with this oil dissolved in 2.5 mL THF, TBAF hydrate (241 mg, 0.92 mmol, 14 eq.), 4A molecular sieves (100 mg), and 3 drops of Et$_3$N sequentially. This solution was left to stir in the dark at room temperature for 8 hours. The reaction mixture was purified directly using silica gel column chromatography (99% ethyl acetate buffered with 1% Et$_3$N) to give 11(a) and 11(b) (15 mg, 38%) as a mixture of diastereomers (1:3.5) which were separated using normal phase HPLC chromatography (90% ethyl acetate/hexanes, buffered with 1% Et$_3$N) to give 2 mg (5%, 3% overall) of the natural A-ring isomer 11(b). 11(a) (1β, 3α): $^1$H NMR (400 MHz, CDCl$_3$) δ 6.41–6.38 (d, J=11.2 Hz, 1H), 6.11–6.08 (m, J=11.2 Hz, 1H), 5.32 (m, 1H), 5.30 (m, 1H), 5.02 (m, 1H), 4.44 (m, 1H), 4.22 (m, 1H), 2.83–2.80 (dm, J=11.6 Hz, 1H), 2.65–1.33 (m, 19H), 1.13 (s, 9H), 1.03–1.01 (d, J=6.8 Hz, 3H), 0.67 (s, 3H); $[\alpha]^D$=4.3; HRMS calcd for C$_{29}$H$_{44}$O$_3$Na [M+Na]: 463.3188, found: 463.3163; II(b) (1α, 3β) $^1$H NMR (400 MHz, CDCl$_3$) δ 6.39–6.36 (d, J=11.2 Hz, 1H), 6.12–6.09 (m, J=11.2 Hz, 1H), 5.34–5.33 (t, J=1.6 Hz, 1H), 5.30–5.29 (t, J=1.4 Hz, 1H), 5.01 (m, 1H), 4.45 (m, 1H), 4.24 (m, 1H), 2.83–2.79 (dm, J=12 Hz, 1H), 2.62–2.58 (dm, J=12.8 Hz, 1H), 2.47–1.33 (m, 18H), 1.12 (s, 9H), 1.03–1.01 (d, J=6.8 Hz, 3H), 0.68 (s, 3H); $^{13}$C NMR (100 MHz, CDCl$_3$) δ 216.1, 159.6, 147.7, 142.6, 132.9, 124.9, 120.3, 116.8, 111.6, 70.6, 66.9, 58.3, 50.1, 45.2, 42.8, 36.6, 36.1, 35.3, 32.7, 29.7, 29.4, 28.8, 26.4, 23.6, 21.9, 21.6, 16.9; IR (neat) 3855, 3752, 3677, 3386, 2924, 2846, 1702, 1654, 1561, 1432, 1362, 1209, 1051, 1010, 846 cm$^{-1}$; UV (MeOH) λ$_{max}$ 264 nm (ε8157); $[\alpha]_D$=+17.2; HRMS calcd for C$_{29}$H$_{44}$O$_3$Na [M+Na]: 463.3188, found: 463.3175. It was possible to separate the diastereomers using normal phase HPLC although optimal separation was obtained only by using very small injections (~200 μg or less).

Example 4

Preparation of Compounds I(a) and I(b)

Anhydrous phosphine oxide (±)-VI (R$^1$, R$^2$=O-OTBDMS) (89 mg, 0.15 mmol, 2 eq.) was dissolved in 2.5 mL distilled THF and cooled to −78° C. Phenyllithium (93 μL of a 1.8M solution in cyclohexane-ether, 0.17 mmol, 2.2 eq.) was added dropwise via syringe resulting in a deep red color. This solution was left to stir for 20 minutes. Anhydrous CD-ring ketone (+)-II (R$^3$=CH$_3$, R$^5$=t-Butyl) (23 mg, 0.08 mmol) was dissolved in 1.5 mL distilled THF and cooled to −78° C. This solution was then added to the reaction mixture via cannula, and the red color persisted. This solution was stirred at −78° C. in the dark for 7 hours at which point it was quenched with saturated potassium carbonate (1 mL) and potassium sodium tartrate (2 mL of a 2M solution). The product was extracted with ethyl acetate (4×60 mL), dried using MgSO$_4$, filtered, concentrated and purified using silica gel column chromatography (3–10% ethyl acetate/hexanes buffered with 1% Et$_3$N) to give a colorless oil. A 5 mL round-bottom flask was charged with a portion of this material (27 mg, 0.04 mmol) dissolved in 2 mL of anhydrous pyridine. Hydroxylamine hydrochloride (III, R$^4$=H) (51 mg, 0.74 mmol, 20 eq.) was added and the reaction was allowed to stir in the dark at room temperature for 24 hours at which point TLC analysis showed complete consumption of starting material and the appearance of a new, more polar product. This material was purified directly using silica gel column chromatography (10% ethyl acetate/hexanes buffered with 1% $Et_3N$) to give a colorless oil. A 5 mL round-bottom flask was charged with this oil dissolved in 2.5 mL THF, TBAF hydrate (135 mg, 0.52 mmol, 14 eq.), 4 Å molecular sieves (60 mg), and 3 drops of $Et_3N$ sequentially. This solution was left to stir in the dark at room temperature for 8 hours. The reaction mixture was purified directly using silica gel column chromatography (99% ethyl acetate buffered with 1% $Et_3N$) to I(a) and I(b) (14 mg, 61%) as a mixture of diastereomers (1:3.5) which were separated using reverse phase HPLC chromatography (38% $H_2O$/acetonitrile) to give 2.3 mg (16%, 5% overall) of I(a) and 4.0 mg (29%, 10% overall) of I(b). I(a) (1β,3α): $^1H$ NMR (400 MHz, $CDCl_3$) δ 6.40–6.37 (d, J=11.2 Hz, 1H), 6.10–6.07 (m, J=11.2 Hz, 1H), 5.32 (m, 1H), 5.29 (m, 1H), 5.02 (m, 1H), 4.45 (m, 1H), 4.22 (m, 1H), 2.83–2.80 (dm, J=11.6 Hz, 1H), 2.64–2.60 (dd, J=12.8 Hz, J=3.4 Hz, 1H), 2.38–1.24 (m, 18H), 1.11 (s, 9H), 1.03–1.01 (d, J=6.8 Hz, 3H), 0.68 (s, 3H); $^{13}C$ NMR (100 MHz, $CDCl_3$) δ 167.7, 159.7, 147.1, 142.7, 132.7, 125.0, 120.3, 116.8, 112.7, 71.4, 66.7, 58.4, 50.0, 45.4, 42.8, 37.4, 37.2, 35.3, 32.6, 29.4, 28.8, 27.7, 26.1, 24.3, 23.6, 21.4, 17.0; $[α]_D$=–3.7; HRMS calcd for $C_{29}H_{45}NO_3Na$ [M+Na]: 478.3297, found: 478.3336; I(b) (1α, 3β) $^1H$ NMR (400 MHz, $CDCl_3$) δ 6.39–6.36 (d, J=11.6 Hz, 1H), 6.12–6.09 (m, J=11.6 Hz, 1H), 5.34–5.33 (t, J=1.6 Hz, 1H), 5.30 (m, 1H), 5.02–5.01 (m, J=1.6 Hz, 1H), 4.44 (m, 1H), 4.24 (m, 1H), 2.83–2.79 (dm, J=12 Hz, 1H), 2.63–2.59 (dm, J=13.6 Hz, 1H), 2.38–1.69 (m, 18H), 1.11 (s, 9H), 1.03–1.02 (d, J=6.8 Hz, 3H), 0.69 (s, 3H); $^{13}C$ NMR (100 MHz, $CDCl_3$) δ 167.7, 159.7, 147.6, 142.7, 132.9, 125.0, 120.3, 116.8, 111.7, 70.7, 66.8, 58.4, 50.0, 45.2, 42.8, 37.4, 37.2, 35.3, 32.6, 29.4, 28.8, 27.7, 26.1, 24.3, 23.6, 21.4, 17.0; IR (neat) 3331, 2955, 2919, 2837, 1661, 1461, 1367, 1349, 1049, 932, 797, 756 $cm^{-1}$; UV (MeOH) $λ_{max}$ 266 nm (ε 8502); $[α]_D$=+4.8; HRMS calcd for $C_{29}H_{45}NO_3Na$ [M+Na]: 478.3297, found: 478.3336.

Example 5

Preparation of Compounds I(c) and I(d)

Anhydrous phosphine oxide (±)-VI ($R^1$, $R^2$=OTBDMS, $R^6$==$CH_2$) (89 mg, 0.15 mmol, 2 eq.) was dissolved in 2.5 mL distilled THF and cooled to –78° C. Phenyllithium (93 μL of a 1.8M solution in cyclohexane-ether, 0.17 mmol, 2.2 eq.) was added dropwise via syringe resulting in a deep red color. This solution was left to stir for 20 minutes. Anhydrous CD-ring ketone (+)-II ($R^3$=$CH_3$, $R^5$=t-Butyl) (23 mg, 0.08 mmol) was dissolved in 1.5 mL distilled THF and cooled to –78° C. This solution was then added to the reaction mixture via cannula, and the red color persisted. This solution was stirred at –78° C. in the dark for 7 hours at which point it was quenched with saturated potassium carbonate (1 mL) and potassium sodium tartrate (2 mL of a 2M solution). The product was extracted with ethyl acetate (4×60 mL), dried using $MgSO_4$, filtered, concentrated and purified using silica gel column chromatography (3–10% ethyl acetate/hexanes buffered with 1% $Et_3N$) to give a colorless oil. A 5 mL round-bottom flask was charged with a portion of this material (12 mg, 0.02 mmol) dissolved in 1.5 mL of anhydrous pyridine. Methoxylamine hydrochloride (III, $R^4$=$CH_3$) (27 mg, 0.33 mmol, 20 eq.) was added and the reaction was allowed to stir in the dark at room temperature. Additional portions of methoxylamine were added (60 eq. Total) and the reaction was stirred for a total of 36 hours. The starting material and the product were very similar in polarity and TLC analysis was not particularly useful for following the reaction. This material was purified directly using silica gel column chromatography (3% ethyl acetate/hexanes buffered with 1% $Et_3N$) to give a colorless oil. A 5 mL round-bottom flask was charged with this oil dissolved in 2 mL THF, TBAF hydrate (59 mg, 0.22 mmol, 14 eq.), 4 Å molecular sieves (60 mg), and 1 drop of $Et_3N$ sequentially. This solution was left to stir in the dark at room temperature for 24 hours. The reaction mixture was purified directly using silica gel column chromatography (99% ethyl acetate buffered with 1% $Et_3N$) to give I(c) and I(d) (6 mg, 59%) as a mixture of diastereomers (1:3.5) which were separated using reverse phase HPLC chromatography (15% $H_2O$/acetonitrile) to give 1.4 mg (19%, 6% overall) of I(c) and 2.8 mg (37%, 12% overall) of I(d). I(c) (1β,3α): $^1H$ NMR (400 MHz, $CDCl_3$) δ 6.41–6.38 (d, J=11.2 Hz, 1H), 6.11–6.08 (m, J=11.6 Hz, 1H), 5.32 (m, 1H), 5.29 (t, J=1.2 Hz, 1H), 5.02 (m, 1H), 4.46–4.44 (m, 1H), 4.24–4.20 (m, 1H), 3.78 (s, 3H), 2.84–2.80 (dm, J=11.8 Hz, 1H), 2.65–2.60 (dd, J=13.0 Hz, 3.8 Hz, 1H), 2.38–1.35 (m, 18H), 1.09 (s, 9H), 1.03–1.01 (d, J=76.8 Hz, 3H), 0.69 (s, 3H); $^{13}C$ NMR (100 MHz, $CDCl_3$) δ 166.8, 159.7, 147.1, 142.7, 132.7, 125.0, 120.3, 116.8, 112.5, 71.4, 66.9, 60.9, 58.3, 50.0, 45.2, 42.8, 37.1, 35.3, 32.6, 29.4, 28.8, 27.8, 26.5, 24.6, 23.6, 21.3, 17.0; $[α]_D$=–2.4; HRMS calcd for $C_{30}H_{48}NO_3$ [M+H]: 470.3634, found: 470.3623; I(d) (1α, 3β) $^1H$ NMR (400 MHz, $CDCl_3$) d 6.39–6.37 (d, J=11.2 Hz, 1H), 6.12–6.09 (m, J=11.2 Hz, 1H), 5.34–5.33 (t, J=1.6 Hz, 1H), 5.29 (t, J=1.2 Hz, 1H), 5.02 (m, 1H), 4.46–4.43 (m, 1H), 4.26–4.23 (m, 1H), 3.78 (s, 3H), 2.84–2.80 (dm, J=11.8 Hz, 1H), 2.63–2.58 (dd, J=13.6 Hz, 3.6 Hz, 1H), 2.38–1.35 (m, 18H), 1.09 (s, 9H), 1.03–1.01 (d, J=7.2 Hz, 3H), 0.69 (s, 3H); $^{13}C$ NMR (100 MHz, $CDCl_3$) d 166.8, 159.7, 147.6, 142.6, 132.9, 124.9, 120.3, 116.8, 111.7, 70.7, 66.8, 60.9, 58.4, 50.0, 45.2, 42.8, 37.1, 35.3, 32.6, 29.7, 29.4, 28.8, 27.8, 26.5, 24.6, 23.6, 21.3, 16.9; IR (neat) 3331, 2955, 2919, 2849, 1461, 1361, 1049, 885 $cm^{-1}$; UV (MeOH) $λ_{max}$ 264 nm (e 6923); $[α]_D$=+6.0; HRMS calcd for $C_{30}H_{48}NO_3$ [M+H]: 470.3634, found: 470.3636.

In a like manner, the following additional compounds were prepared:

Compounds I(e) and I(f): By replacing methoxylamine hydrochloride (III, $R^4$=$CH_3$) with O-ethylhydroxylamine hydrochloride (III, $R^4$=Et). The crude reaction product was purified by a column chromatography eluted with 99% ethyl acetate in the presence of 1% triethylamine to afford 4.8 mg of a mixture of diastereomers I(e) (1α, 3β) and I(f) (1β,3α) in 63% yield and in a ratio of 1.8:1, respectively. This diastereomeric mixture was then separated by HPLC (Phenomenex Luna column, reserve phase, 3 mL/min) eluted with 15% water in acetonitrile to afford 1.2 mg I(e) (1α, 3β) and 0.6 mg 1(f) (1β,3α) in 16% and 8% yields, respectively. Retention time for I(e) (1α, 3β) is 55.48 min. and for 1(f) (1β,3α) is 53.23 min. Data for I(e) (1α, 3β): $[α]^{25}_D$=+4.66 (c=0.01, $CHCl_3$) $^1H$ NMR ($CDCl_3$, 400 MHz): δ 6.38 (d, 1H, J=10.8 Hz), 6.11 (d, 1H, J=11.6 Hz), 5.34–5.30 (m, 2H), 5.02 (d, 1H, J=1.2 Hz), 4.44 (m, 1H), 4.24 ((m, 1H), 4.03 (q, 2H, J=7.2 Hz), 2.84–2.79 (m, 1H), 2.62–2.59 (m, 1H), 2.39–2.30 (m, 2H), 2.23–1.87 (m, 7H), 1.79–1.66 (m, 4H), 1.56–1.38 (m, 6H), 2.21 (t, 3H, J=7.2 Hz), 1.09 (s, 9H), 1.02 (d, 3H, J=6.8 Hz), 0.69 (s, 3H). $^{13}C$ NMR ($CDCl_3$, 100 MHz): δ 166.40, 159.78, 147.65, 142.70, 132.88, 124.99, 120.27, 116.84, 111.61, 70,68, 68.49, 66.88, 58.44, 50.03, 45.17, 42.86, 37.18, 37.15, 35.35, 32.55, 29.37, 28.79, 27.85, 26.52, 24.59, 23.63, 21.34, 16.97, 14.64. IR (Thin Film) 3345 (br, m), 2928 (s), 1666 (w), 1462

(w), 1365 (w), 1092 (w), 1053 (s), 916 (w), 873 (w), 801 (w) cm$^{-1}$. HRMS: calculated for $C_{31}H_{49}NO_3Na^+$ [M+Na]: 506.3604 Found: 506.3604. Data for 1(f) (1β,3α) was not obtained due to insufficient amount of compound.

Compounds I(i) and 1(h): By replacing methoxylamine hydrochloride (III, $R^4$=CH$_3$) with O-allylhydroxylamine hydrochloride (III, $R^4$=allyl). The crude reaction product was flash column chromatography eluted with 99% ethyl acetate in the presence of 1% triethylamine afforded 6.1 mg of a mixture of diastereomers I(g) (1α, 3β) and 1(h) (1β,3α) in 73% yield and in a ratio of 2.0:1, respectively. This diastereomeric mixture was then separated by HPLC (Phenomenex Luna column, reserve phase, 3 mL/min) eluted with 15% water in acetonitrile to afford 1.1 mg I(g) (1α, 3β) and 0.53 mg 1(h) (1β,3α) in 13% and 6% yields, respectively. Retention time for I(g) (1α, 3β) is 55.55 min. and for I(h) (1β,3α) is 53.19 min. Data for I(g) (1α, 3β) MK-1625 (NOAll)-TB-2: $[\alpha]^{25}D$=+4.0 (c=0.01, CHCl$_3$) $^1$H NMR (CDCl$_3$, 400 MHz): δ 6.38 (d, 11H, J=11.2 Hz), 6.11 (d, 11H, J=11.2 Hz), 6.02–5.92 (m, 1H), 5.34–5.29 (m, 1H), 5.26–5.22 (m, 1H), 5.16–5.13 (m, 1H), 5.02 (br, 1H), 4.50–4.48 (m, 2H), 4.44 (br, 1H), 4.24 (br, 1H), 3.50 (br, 2H), 2.83–2.79 (m, 1H), 2.62–2.59 (m, 1H), 2.38–2.30 (m, 2H), 2.24–1.87 (m, 9H), 1.79–1.76 (m, 3H), 1.52–1.30 (m, 2H), 2.21 (t, 3H, J=7.2 Hz), 1.09 (s, 9H), 1.02 (d, 3H, J=6.8 Hz), 0.68 (s, 3H). $^{13}$C NMR (CDCl$_3$, 100 MHz): δ 166.88, 159.74, 147.66, 142.72, 134.90, 132.87,124.99, 120.28, 116.82, 116.36, 111.60, 74.07, 70,69, 66.89, 54.43, 50.03, 45.18, 42.87, 37.17, 35.35, 32.58, 29.70, 29,36, 28.79, 27.81, 26.61, 24.62, 23.63, 21.40, 16.96. IR (Thin Film) 3353 (br, m), 2926 (s), 1668 (sh, w), 1462 (m), 1365 (m), 1261 (w), 1092 (w), 1048 (br, m), 915 (m), 802 (w), cm$^{-1}$. HRMS: calculated for $C_{32}H_{49}NO_3Na^+$ [M+Na]: 518.3604 Found: 518.3572. Data for 1(h) (1β,3α(x) MK-1625 (NOAII)-TB-1 was not obtained due to insufficient amount of compound.

Compounds I(i) and I(j): By replacing methoxylamine hydrochloride (III, $R^4$=CH$_3$) with O-phenylhydroxylamine hydrochloride (III, $R^4$=phenyl). The crude reaction product was flash column chromatography eluted with 99% ethyl acetate in the presence of 1% triethylamine afforded 11.8 mg of a mixture of diastereomers I(i) (1α, 3β) and I(j) (1β,3α) in 83% yield and in a ratio of 1.8:1, respectively. This diastereomeric mixture was then separated by HPLC (Phenomenex Luna column, reserve phase, 3 mL/min) eluted with 15% water in acetonitrile to afford 5.3 mg I(i) (1α, 3β) and 2.8 mg I(j) (1β,3α) in 37% and 20% yields, respectively. Retention time for I(i) (1α, 3β) is 67.86 min. and for I(j) (1β,3α) is 64.85 min. Data for I(i) (1α, 3β): $[\alpha]^{25}D$=+0.31 (c=0.25, CHCl$_3$) $^1$H NMR (CDCl$_3$, 400 MHz): δ 7.30–7.26 (m, 2H), 7.16–7.13 (m, 2H), 6.98–6.94 (m, 1H), 6.37 (d, 1H, J=11.2 Hz), 6.09 (d, 1H, J=11.2 Hz), 5.34 (dd, 1H, J=1.6 Hz, J=1.6 Hz), 5.31–5.30 (m, 1H), 5.02–5.01 (m, 1H), 4.45–4.44 (m, 1H), 4.24–4.23 (m, 1H), 2.80 (dd, 1H, J=4 Hz, J=12 Hz), 2.60 (dd, 1H, J=3.6 Hz, J=13.6 Hz), 2.37–2.30 (m, 4H), 2.20–2.13 (m, 2H), 2.07–1.87 (m, 3H), 1.78–1.44 (m, 9H), 1.20 (s, 9H), 1.03 (d, 3H, J=6.8 Hz), 0.68 (s, 3H). $^{13}$C NMR (CDCl$_3$, 100 MHz): δ 170.34, 159.75, 159.57, 147.62, 132.89, 129.13, 124.95, 121.36, 120.41, 116.83, 114.33, 111.63, 70.69, 66.88, 58.42, 50.03, 45.17, 42.85, 37.99, 37.13, 35.32, 32.55, 29.34, 28.76, 27.73, 27.03, 24.87, 23.61, 21.42, 17.00. IR (Thin Film) 3357 (br, m), 2928 (s), 2856 (sh, m), 1590 (s), 1489 (sh, s), 1394 (m), 1219 (br, s), 1158 (w), 1052 (br, m), 1023 (w), 956 (m), 910 (s) cm$^{-1}$. HRMS: calculated for $C_{35}H_{49}NO_3Na^+$ [M+Na]: 554.3604 Found: 554.3601. Data for 1(j) (1β,3α): $[\alpha]^{25}D$=-24.35 (c=0.27, CHCl$_3$) $^1$H NMR (CDCl$_3$, 400 MHz): δ 7.30–7.26 (m, 2H), 7.16–7.13 (m, 2H), 6.98–6.94 (m, 1H), 6.39 (d, 1H, J=11.2 Hz), 6.08 (d, 1H, J=11.6 Hz), 5.32–5.30 (m, 2H), 5.01 (d, 1H, J=1.6 Hz), 4.45 (br, 1H), 4.23–4.21 (m, 1H), 2.81 (dd, 1H, J=4.4 Hz, J=12 Hz), 2.63 (dd, 1H, J=3.6 Hz, J=13.2 Hz), 2.37–2.27 (m, 3H), 2.19–2.13 (m, 2H), 2.06–1.89 (m, 3H), 1.78–1.75 (m, 3H), 1.64–1.44 (m, 7H), 1.20 (s, 9H), 1.04 (d, 3H, J=6.8 Hz), 0.68 s, 3H). $^{13}$C NMR (CDCl$_3$, 100 MHz): δ 170.34, 159.75, 159.57, 147.08, 142.68,132.71, 129.13, 124.99, 121.37, 120.41, 116.83, 114.33, 112.82, 71.51, 66.76, 58.41, 50.03, 45.51, 42.77, 37.99, 37.13, 35.30, 32.55, 29.38, 28.74, 27.73, 27.03, 24.86, 23.59, 21.39, 17.02. IR (Thin Film) 3350 (br, m), 2926 (s), 2850 (m), 1590 (m), 1490 (m), 1220 (br, s), 1158 (w), 1050 (br, m), 910 (s) cm$^{-1}$. HRMS: calculated for $C_{35}H_{49}NO_3Na^+$ [M+Na]: 554.3604 Found: 554.3578.

Example 6

Preparation of Compound I(k)

A solution of 53 mg (0.094 mmol) of 19-nor-phosphine oxide VI ($R^1$, $R^2$=OTBDMS, $R^6$=H) in 2.0 mL of anhydrous THF was cooled to −78° C. and treated with 59 μL (0.094 mmol, 1.6 M in hexanes) of n-BuLi under argon atmosphere. The mixture turned deep reddish and was stirred for 15 min at −78° C. To the solution was added dropwise a precooled (−78° C.) solution of 10 mg (0.031 mmol) of the C,D-ring ketone V ($R^3$=CH$_3$, $R^5$=t-butyl, see Example 2) in 1.5 mL of anhydrous THF via cannula. The reaction kept going until the reddish orange color faded to yellow (about 2 hr). The reaction was quenched by adding 1.0 mL of pH 7 buffer at −78° C., then warmed to room temperature, extracted with EtOAc (20 mL×2), washed with brine, dried over MgSO$_4$, concentrated. The residue was subjected to column chromatography with EtOAc/hexanes (1/15) as eluent to afford 11 mg (52%) of the coupled product as a colorless oil.

The coupled product (10 mg, 0.015 mmol) was dissolved in 1.0 mL of anhydrous pyridine, and to this solution was added O-ethylhydroxylamine hydrochloride (26 mg, 20 eq.) and 4A powdered molecular sieves (10 mg) at room temperature. The mixture solution was then stirred at room temperature for 20 hr. Reaction was monitored by TLC. This reaction mixture was then directly subjected to column chromatography with EtOAc/hexanes (1/15) as eluent to afford 10 mg (97%) of oxime product as a colorless oil.

The oxime product (8.9 mg, 0.013 mmol) was dissolved in 2 mL of anhydrous THF, and to the solution was added 0.19 mL (0.19 mmol) of a 1.0 M solution of TBAF in THF. The resulting mixture was stirred overnight at room temperature, then quenched with 2 mL of water. The solution was extracted with EtOAc (20 mL×3), washed with brine, dried over MgSO$_4$, concentrated. The residue was subjected to column chromatography with EtOAc as eluent to give 5.6 mg (94%) of the crude product of (−)-1(k) as a colorless oil. The crude product (4 mg out of 5.6 mg) was purified by reverse-phase HPLC (C-18 semipreparative column, 18% H$_2$O in MeCN, 3 ml/min) to afford 2.5 mg of (−)-1(k) (1α, 3β, $t_R$=38.7 min).: $[\alpha]^{24}{}_D$=−47.2 (c=0.023, CHCl$_3$). $^1$H NMR (400 MHz, CDCl$_3$) δ 6.31 (d, J=11.2 Hz, 1H), 5.95 (d, J=11.2 Hz, 1H), 5.31 (m, 1H), 4.13 (m, 1H), 4.06 (m, 1H), 3.78 (s, 3H), 2.75–2.81 (m, 2H), 2.49 (dd, J=13.6, 3.6 Hz, 1H), 2.38 (dd, J=11.2, 5.6 Hz, 1H), 2.10–2.29 (m, 6H), 1.94–2.06 (m, 2H), 1.36–1.82 (m, 12H), 1.09 (s, 9H), 1.02 (d, J=6.8 Hz, 3H), 0.69 (s, 3H). $^{13}$C NMR (100 MHz, CDCl$_3$) δ 166.8, 159.9, 142.6, 131.1, 123.8, 120.3, 115.1, 67.4, 67.2, 61.0, 58.4, 49.9, 44.6, 42.2, 37.2, 37.1, 35.3, 32.6, 29.4, 28.6, 27.8, 26.5, 24.6, 23.5, 21.3, 27.1. IR (neat, cm$^{-1}$) 3355, 2930, 1668, 1463, 1364, 1054, 976, 886, 810. HRMS ([M+Na]$^+$) calcd. 480.3448, found 480.3427.

Example 7

CYP24 Enzyme Assay (Induced KPK1A-ras Cells)

(i) Material and Reagents:

1,25(OH)$_2$D$_3$ 10$^{-5}$ M

[$^3$H]-1,25(OH)$_2$D$_3$ 25,000 CPM/µL

HPK1A-ras cells 48-well plate

Methanol

Dichlorimethane

Saturated KCI:KCI 30 g, H$_2$O400 ml (ii) Procedure:

1. Induction of HPK1A-ras cells (The day before assay)
   When the HPK1A-ras cells were 80–90% confluent, add 1 µL 10$^{-5}$ M 1,25(OH)$_2$D$_3$ to 1 mL medium in the plate (final concentration is 10$^{-8}$ M).

2. Preparation of cell suspension
   After 18 to 20 hours induction, removed the medium and washed the cell twice with PBS. Then tripsinized the cells from plate, centrifuge (2,000 rpm, 5 min) and suspended cells pellet in DMEM medium+1% BSA.
   Counted the cells and adjust cells density to 250,000/150 µL, add 150 µL cell suspension to each well in 48-well plate. (including 3 wells as no cell control, and 3 well cells without drug or inhibitor as control).

3. Added 25 µL ketoconazole (final concentration 10$^{-5}$ M, 10$^{-6}$ M, 10$^{-7}$ M, 10$^{-8}$ M) or drugs into each designated well. Keep the plate in 37° C. for 10 min.

4. Preparation of substrate
   Took certain amount of DMEM+1% BSA medium (25*Well number+200)µL to a tube, added certain amount of $^3$H-1,25(OH)$_2$D$_3$ (well number+2) µL and certain amount of 100 mM DPPD (well number/5)µL and mixed them by vortex.

5. Incubation
   Added 25 µL substrate to each well, incubated the plate at 37° C. for 3 hour.
   Added 25 µL substrate to counting plate (2 well) as a total count.

6. Lipid extraction and counting
   Added 500 µL methanol to each well to stop the reaction, transfered them to tube
   Added 250 µL dichloromethane and vortex.
   Added 250 µL dichloromethane and 250 µL saturated KCI, and vortexed.
   Centrifuged at 4000 rpm for 5 min.
   Transfered 100 µL of aqueous phase (upper phase) to counting plastic counting plate. Added 600 µL of scintillation fluid to each well. Counted the plate in scintillation counter.

7. Calculation enzyme activity
   CPM of cell control after subtraction of CPM of NCC is as 100% enzyme activity.
   Enzyme activity=(CPM in test compounds well−CPM in NCC well)/(CPM in Cell control−CPM in NCC well)* 100%

Dilution of Ketoconazole

Stock 10$^{-2}$ M

| Concentration (final) | From previous step | DMEM + 1% BSA | Concentration (actual) |
|---|---|---|---|
| 10$^{-5}$ M | 4 | 496 | 8 * 10$^{-5}$ M |
| 10$^{-6}$ M | 12.5 | 112.5 | 8 * 10$^{-6}$ M |
| 10$^{-7}$ M | 12.5 | 112.5 | 8 * 10$^{-7}$ M |
| 10$^{-8}$ M | 12.5 | 112.5 | 8 * 10$^{-8}$ M |

Dilution of test compounds

Stock 10$^{-3}$ M

| Concentration (final) | From previous step (µL) | DMEM + 1% BSA (µL) | Concentration (actual) |
|---|---|---|---|
| 10$^{-5}$ M | 10 | 115 | 8 * 10$^{-5}$ M |
| 10$^{-6}$ M | 12.5 | 112.5 | 8 * 10$^{-6}$ M |
| 10$^{-7}$ M | 12.5 | 112.5 | 8 * 10$^{-7}$ M |
| 10$^{-8}$ M | 12.5 | 112.5 | 8 * 10$^{-8}$ M |

(iii) Results:

Compounds of Formula I(a), I(c), I(e), I(g), I(i) and I(k) showed significantly greater inhibition of CYP24 than ketoconazole. A graph showing inhibition of CYP24 activity by compounds I(a) and I(c) (indicated as BH1625(NOH)-TB-2 (CTA062) and BH-1625(NOMe)-TB-2-(CTA065) respectively) compared to ketoconazole is shown in FIG. 1A.

(iv) References:

Ray S, Ray R, Holick M. Metabolism of $^3$H-1alpha, 25-dihydroxyvitamin D$_3$ in the cultured human keratinocytes (1995) 59:117–122

Dilworth F J, Scott I, Green A, Strugnell S, Guo Y D, Roberts E A, Kremer R, Calverley, M J, Makin H L J, Jones G. Different mechanisms of hydroxylation site selection by liver and kidney cytochrome P450 species (CYP27 and CYP24) involved in Vitamin D metabolism. (1995) J Biochem 270(28):16766–16774

Example 8

Assay of CYP1-alpha hydroxylase (Using Transfected COS-1 Cells)

(A) Transit Transfection (i) Reagent and Material

1. COS-1 cells (50–80% confluent)
2. FuGene 6 Transfection Reagent
3. PcDNA vector containing CYP-1alpha hydroxylase cDNA(1 µg/µl)
4. DMEM Medium+10% FCS
5. DMEM Medium (serum-free)
6. 6-well plate (ii) Transfection Cocktail Preparation (The Amount Depended on how Many Wells Transfected)

1. To a sterile tube, added serum-free medium (100 µl per well), then added FuGene 6 Reagent (3 µl per well). Tapped gently to mix. Payed attention to the order. Added FuGene 6 Reagent directly to medium, did not allow undiluted Fugene 6 Reagent to come in contact with plastic surfaces other than the pipette tip.

2. Added DNA solution (1 µg per well) to the prediluted FuGene 6 Reagent from step 2

3. Gently tapped the tube to mix the contents. Did not vortex. Incubated for 15 min at room temperature (no more than 45 min).

(iii) Cells Preparation

1. Trypsinized Cos-1 cells, centrifuged cell suspension, suspended cells pellet in DMEM medium+10% FCS.
2. Diluted the cells suspension to 750,000 cell/ml (75 cell/square), (iv) Transfection.

1. Added 1.7 ml DMEM medium+10% FCS to each well of 6 well plate.
2. Transferred the correct volume of the cell suspension (200 μl/well) to the transfection cocktail. Mixed gently.
3. Added 0.3 ml of the mixture to each well. Made sure that the same amount cells were added to each well. Swirled the wells to ensure even dispersal.
4. Incubated the cells for 24 hours at 37° C., 5% $CO_2$ until enzyme activity assay.

(B) Enzyme Activity Assay (i) Reagent and Materials

DMEM medium+1% BSA
PBS
$[^3H-26,27]-25(OH)D_3$
DPPD 100 mM (ii) Procedure

1. Washed cells once with PBS. Took care no to disturb the attached cells.
2. Added 0.55 ml medium (DMEM+1% BSA) each well.
3 Added 0–025 ml medium containing test compounds.
4. Incubated the cells for 10 minutes.
5. Added 0.025 ml medium containing $[^3H-26,27]-25(OH)D_3$ (50,000 CPM) and DPPD (0.6 μl stock).
6. Incubated the cells for 2 hour.
7. Added 1.5 ml Methanol to stop reaction.
8. Added internal standard.
9. Transferred the medium to labeled tube.
10. Added 0.75 ml dichloromethane, vortexed and kept in room temperature for 15 minutes.
11. Added 0.75 ml dichloromethane and 0.75 ml saturated KCl.
12. Vortexed and centrifuged.
13. Removed upper phase and dried the lower phase in Speed-Vac.
14. Added 110 μl mobile phase, vortexed and centrifuged for 5 min.
15. Transferred 105 μl to the insert in HPLC vial.
16. HPLC analysis conditions:
   Solvent: Hexane/isopropanol/methanol (91/7/2)
   Column: SIL 3 μm column
   Flow rate: 2 ml/min
   Detector: UV detector and radioactive detector.

Figure 1B:
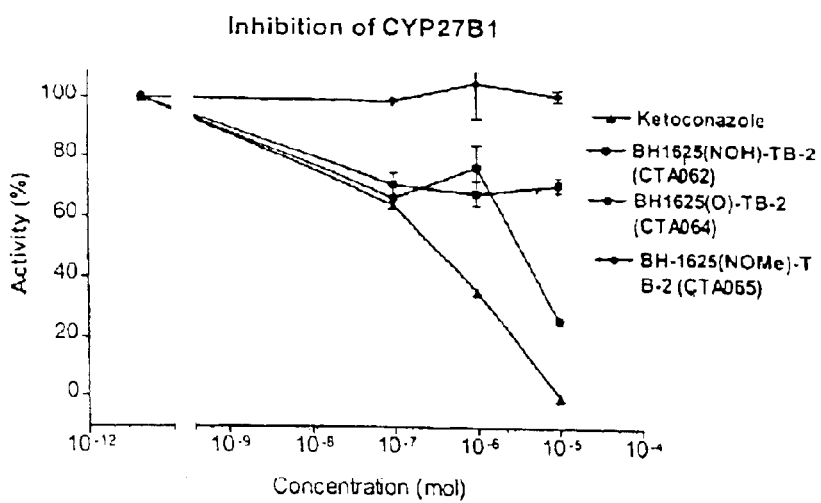
FIG. 1B is a graph showing the inhibition of CYP27B1 activity by compounds I(a) and I(c) (indicated as BHI 1625(NOH)-TB-2 (CTA062) and BH-1625(NOMe)-TB-2-(CTA065) respectively) compared to ketoconazole.

(C) Results:

Compounds of Formula I(a), I(c), I(e), I(g), I(i) and I(k) showed little to no ($IC_{50}$>10,000 nM) inhibition of CYP27B1. A graph showing the inhibition of CYP27B1 activity by compounds I(a) and I(c) (indicated as BH1625 (NOH)-TB-2 (CTA062) and BH-1625(NOMe)-TB-2-(CTA065) respectively) compared to ketoconazole is shown in FIG. 1B.

(D) References

Shink T, Shimada H, Wakino S, Anazawa H, Hayashi M, Saruta T, Deluca H, Suda T. Cloning and expression of rat 25-hydroxyvitamin $D_3$-1alpha-hydroxylase cDNA. (1997) Pro. Natl Acad Sci 94:12920–12925 Muralidharan K R Rowland-goldsmith M, Lee S A, Park G, Norman A W, Henry H L, Okamura W H. Inhibitors of 25-hydroxyvitamin $D_3$-1alpha-hydroxylase: Thiavitamin D analogues and biological evaluation. (1997) J Steroid Biochem. Molec. Biol. 62(1):73–78.

Example 9

CYP27A1 Enzyme Assay (A) Procedure:
As described in:

Dilworth F J, Black S M, Guo Y D, Miller W L, Jones G. Construction of a P450c27 fusion enzyme: a useful tool for analysis of vitamin $D_3$ 25-hydroxylase (1996) Biochem J 320:267–271

Sawada N, Sakaki T, Ohta M, Inouye K. Metabolism of vitamin D (3) by human CYP27AI (2000) Biochem Biophys Res Commun 273(3):977–84

Figure 1C:
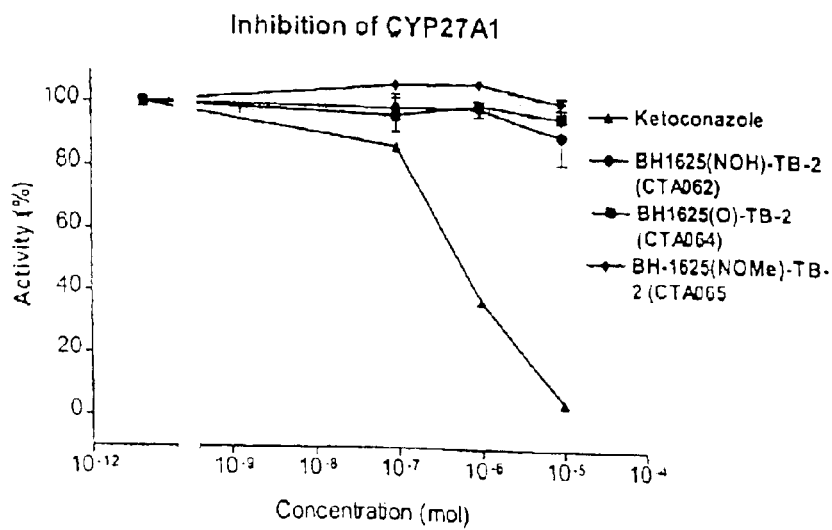
FIG. 1C is a graph showing the inhibition of CYP27A1 activity by compounds I(a) and I(c) (indicated as BH1625 (NOH)-TB-2 (CTA062) and BH-1625(NOMe)-TB-2-(CTA065) respectively) compared to ketoconazole.

(B) Results:

Compounds of Formula I(a), I(c), I(e), I(g), I(i) and I(k) showed little to no ($IC_{50}$>10,000 nM) inhibition of CYP27A1. A graph showing the inhibition of CYP27A1 activity by compounds I(a) and I(c) (indicated as BH1625 (NOH)-TB-2 (CTA062) and BH-1625(NOMe)-TB-2-(CTA065) respectively) compared to ketoconazole is shown in FIG. 1C.

Example 10

VDR Binding Assay (A) Reagent and materials

1. VDR 9.3 pmol/μl (human, recombinant, Biomol).
2. $[^3H]-1,25(OH)_2D_3$ in ethanol
3. $1,25(OH)_2D_3$ in ethanol
4. $TEK_{300}$

| Tris-HCl | 50 mM |
|---|---|
| EDTA | 1.5 mM |
| KCl | 300 mM |
| Adjusted pH to 7.4 (25° C.) | |

5. $TEDK_{300}$
   $TEK_{300}$
   DTT (dithiothreitol) 10 mM (MW 154.24)
6. Tris buffer
   22.50 a Tri-HCl
   500 ml $H_2O$
   13.25 g Tris-base
   500 ml $H_2O$
   Kept in 4° C.
7. Dextran-T70 (Mol 70,000) Pharmacia
8. Charcoal (carbon decolorizing neutral, norit) Fishery
9. Gelatin (G-2625 Sigma)

(B) Reagent Preparation

1. Charcoal dextran solution (1) Tris buffer
    Mixed equal amount of Tris-HCl and Tris-base.
(2) Norit decolorizing neutral charcoal    2.0 g -continued

| | | |
|---|---|---|
| | Tris buffer | 150 mL |
| | Stirred | |
| (3) | Dextran T - 70 | 0.2 g |
| | Tris buffer | 50 ml. |
| (4) | Slowly dripped the suspended dextran into charcoal solution with stirring. | |
| | Kept in refrigerate overnight. | |
| | Thirty minutes before use, stored on ice with continuous mixing | |

2. TEK$_{300}$/Gelatin solution 50 mg swine gelatin 5 ml TEDK$_{300}$ solution heated, stirred then cooled to 4° C.

5 ml TEDK$_{300}$ solution

3. Preparation of 1,25(OH)$_2$D$_3$ and test compounds in ethanol 1,25(OH)$_2$D$_3$: 125, 250, 500, 1000, 2000, 4000 pg/25 µl. (stock $10^{-5}$ M/25 µL 100,000 pg/25 µL)

Test compounds: 12,500, 25,000, 50,000, 100,000, 200,000 and 400,000 pg/25 µL. (4*10–5M/25 µL=400,000 pg/25 µL)

| Label | Concentration (ng/mL) | Amount (pg/50 µL) |
|---|---|---|
| | 5.0 | 125 |
| Std F | 10.0 | 250 |
| Std G | 20.0 | 500 |
| Std H | 40.0 | 1000 |
| | 80.0 | 2000 |
| Std I | 160.0 | 4000 |

4. Dilution of VDR:

1 µl stock VDR in 2.5 ml TEDK$_{300}$/Gelatin solution (500 µl/tube), (kept on ice)

(C) Assay:

| label | Standards | NSB buffer | VDR | 1 h RT | $^3$H-1.25(OH)$_2$D$_3$ | 1 h RT | Reagent C-charcoal | On ice 30 min | Spin at 4° C. |
|---|---|---|---|---|---|---|---|---|---|
| TC (Total) | 25 µL reagent D | 100 µL reagent L | 500 µL reagent A | | 50 µL reagent B mixed all tubes | | 100 µL reagent C mixed all tubes | | 2000 rpm. 10 min Added 100 µl to counting rack Counted 5–10 min |
| NSB (non-specific b) | | 500 µL reagent L | | | | | | | |
| Max b$_0$ binding | | | 500 µL reagent A mixed all tubes | | | | | | |
| Standard | 25 µL of each standard | | | | | | | | |
| Test | 25 µL of each concentration of sample | | | | | | | | |

(D) Calculations:

The amount of 1,25(OH)$_2$D$_3$ to displace 50 percent [$^3$H]-1,25(OH)$_2$D$_3$ from VDR is calculated as B$_{50}$ for 1,25(OH)$_2$D$_3$. The VDR binding of other compounds is calculated as B$_{50}$ relative to a value of 1 for 1,25(OH)$_2$D$_3$.

Dilution of 1,25(OH)D$_3$

| Concentration (pg/25 ul) | Final concentration M | $10^{-5}$ M | Ethanol (ul) |
|---|---|---|---|
| 4,000 | 2 * $10^{-8}$ | 6 | 144 |
| 2,000 | $10^{-8}$ | 70 | 70 |
| 1,000 | 5 * $10^{-9}$ | 70 | 70 |
| 500 | 2.5 * $10^{-9}$ | 70 | 70 |
| 250 | 1.25 * $10^{-9}$ | 70 | 70 |
| 125 | 6.25 * $10^{-10}$ | 70 | 70 |

Dilution of test compounds

| Concentration (pg/50 ul) | Final concentration M | $10^{-3}$ M | Ethanol |
|---|---|---|---|
| 400,000 | 2 * $10^{-6}$ | 6 | 144 |
| 200,000 | $10^{-6}$ | 70 | 70 |
| 10,000 | 5 * $10^{-7}$ | 70 | 70 |
| 5,000 | 2.5 * $10^{-7}$ | 70 | 70 |
| 25,000 | 1.25 * $10^{-7}$ | 70 | 70 |
| 12,500 | 6.25 * $10^{-8}$ | 70 | 70 |

Figure 2:
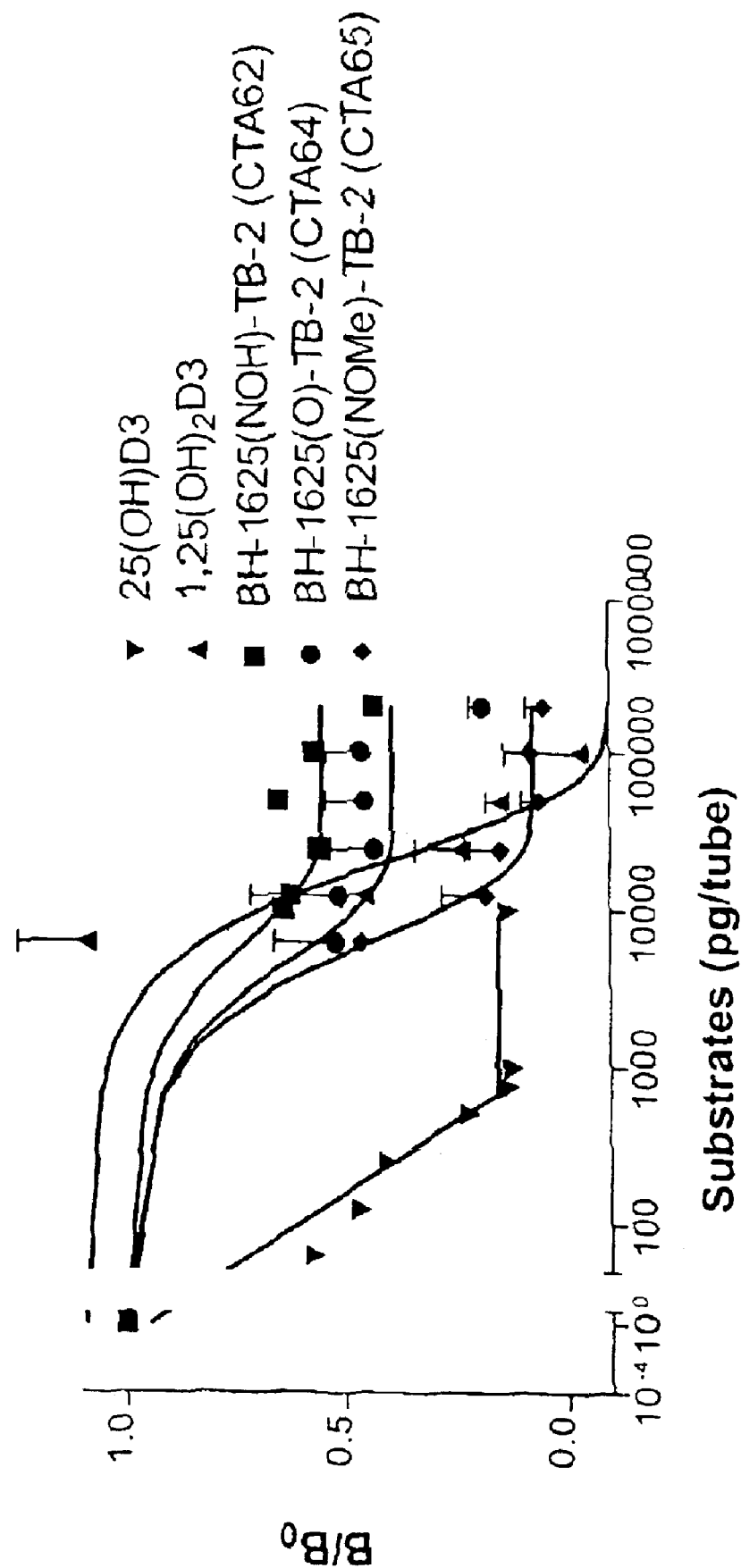
FIG. 2 is a graph showing the binding of compounds I(a) and I(c), (indicated as BH-1625(NOH)-TB-2 (CTA62) and BH-1625(NOMe)-TB-2-(CTA65) respectively) to transporter D protein (DBP) compared to 1α,25-dihydroxy vitamin $D_3$ and 25-hydroxy vitamin $D_3$.

(E) Results:

A graph showing the binding of compounds I(a) and I(c), (indicated as BH-1625(NOH)-TB-2 (CTA62) and BH-1625 (NOMe)-TB-2-(CTA65) respectively) to transporter D protein (DBP) compared to 1α,25-dihydroxy vitamin D$_3$ and 25-hydroxy vitamin D$_3$ is shown in FIG. 2.

(F) References:

1. Ross T K, Prahl J M, DeLuka H. Overproduction of rat 1,25-dihydroxyvitamin D$_3$ receptor in insect cells using the baculovirus expression system. (1991) Proc Natl Acd Sci USA 88:6555–6559

2. Wecksler W R, Norman A W. An hydroxylapatite batch assay for the quantitation of 1alpha, 25-dihydroxyvitamin D$_3$-receptor complexes (1979) Anal Biochem 92:314–323

Example 11

Transcriptional Activity Assay (A) Reagent and Materials:

pSG5-hVDR1/3 from DRs. Mark Haussler and Kerr Whitfield, (University of Arizona, Tucson, Ariz.); hVDR1/3 DNA inserted into the EcoRI site of pSG5 vector (CT4)[4]TKGH from DRs. Mark Haussler and Kerr Whitfield, (University of Arizona, Tucson, Ariz.); Four copies of the CT4 synthetic rat osteocalcin VDRE ligated and annealed into pTKGH vector which has a thymidine promoter linked to the human GH gene.

hGH ELISA kit. Boehringer Mannheim
Fugene 6 transfection reagent
COS-1 cells
DMEM medium and DMEM medium+10% FCS
1,25(OH)$_2$D$_3$ and test compounds (B) Transfection:
1. Subcultured COS cells into 24-well plate (5,000 cell1/well) one day before transfection.
2. Cocktail preparation (the amount depended on how may wells transfected).
    (1) To a sterile tube, added serum-free medium (100 μl per well), then added FuGene 6 Reagent (0.6 μl per well). Tapped gently to mix. Payed attention to the order. Added FuGene 6 Reagent directly to medium, did not allow undiluted Fugene 6 Reagent to come in contact with plastic surfaces other than the pipette tip.
    (2) Added DNA solution (pSG5-hVDR1/3 and (CT4)$^4$TKGH vectors) (0.1 μg each per well) to the pre-diluted FuGene 6 Reagent from step 2
    (3) Gently tapped the tube to mix the contents. Did not vortex. Incubated for 15 min at room temperature (no more than 45 min).
3. Removed the medium and replaced by 0.4 ml fresh medium
4. Added the 100 μl cocktail to each well in drop-wise manner.

(C) Treatment of Transfected Cells with Different Concentrations of 1,25(OH)$_2$D$_3$ and Test Compounds:
30 min to 1 hour after transfection, 1,25(OH)$_2$D$_3$ (as control) and test compounds were added to the medium in 20 μl medium. The concentration range for 1,25(OH)$_2$D$_3$ was $10^{-10}$ to $10^{-8}$ M ($10^{-10}$, $3*10^{-9}$, $10^{-9}$, $3*10^{-8}$, $10^{-8}$ M) and for test compounds was from $3*10^{-9}$M to $10^{-7}$M ($3*10^{-9}$, $10^{-9}$, $3*10^{-8}$, $10^{-8}$, $3*10^{-8}$, $10^{-7}$ M). Incubation continued for 24 hours.

(D) Measurement of GH Content in Medium:
After 24 hour incubation, 200 μL diluted aliquots of medium (dilution of 20–50 times) were used for human GH determination. Sample was assayed according to instruction of hGH ELISA kit.

Figure 3:
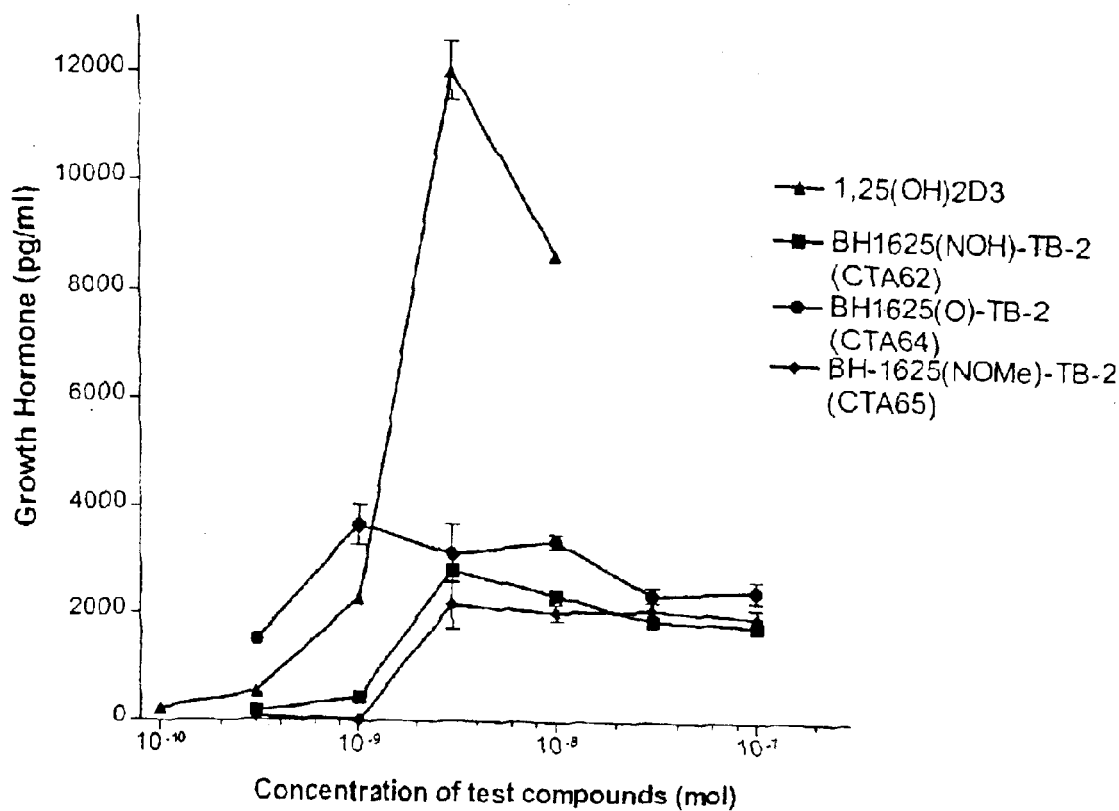
FIG. 3 is a graph showing the activity of compounds I(a) and I(c) (indicated as BH1625(NOH)-TB-2 (CTA62) and BH-1625(NOMe)-TB-2-(CTA65) respectively) in the vitamin D transcription assay compared to 1α,25-dihydroxy vitamin $D_3$.

(E) Results:
A graph showing the activity of compounds I(a) and I(c) (indicated as BH1625(NOH)-TB-2 (CTA62) and BH-1625(NOMe)-TB-2-(CTA65) respectively) in the vitamin D transcription assay compared to 1α,25-dihydroxy vitamin D$_3$ is shown in FIG. 3.

(F) References
Hashimoto Y, Ikeda I, Ikeda M, Takahashi Y, Hosaka M, Uchida H, Kono N, Fukui H, Makino T, Honjo M. Construction of a specific and sensitive sandwich enzyme immunoassay for 20 KD human growth hormone (1998) J Immunol Methods 221:77–85
Jone G, Byford V, Makin H L J, Kremer R, Rice R H, deGraffenried L A, Knutson J C, Bishop C W. Anti-proliferative activity and target cell catabolism of the vitamin D analogue 1 alpha, 24(OH)$_2$D2 in normal and immortalized human epidermal cells (1996) Biochem Pharmacol 52:133–140

Example 12

DBP Binding Assay (Human Plasma)

(A) Reagents:
1. Tris buffer:
    22.50 g Tris-HCl
    500 ml H$_2$O
2. 13.25 g Tris-base
    500 ml H$_2$O
    Kept in 4° C.
3. Dextran-T70 (Mol 70,000) Pharmacia
4. Charcoal (carbon decolorizing neutral, norit) Fishery
5. DBP (vitamin D binding protein) (human plasma)
6. [$^3$H] 25(OH)D$_3$
7. Gelatin (G-2625 Sigma)

(B) Reagent Preparation:
1. Tris buffer
    Mixed equal volume of two Tris buffer.
2. Dextran coated charcoal solution

| (1) | preparation of charcoal solution | |
|---|---|---|
| | Norit decolorizing neutral charcoal | 2.0 g |
| | Tris buffer | 150 mL |
| | Stirring | |
| (2) | preparation of dextran solution | |
| | Dextran T - 70 | 0.2 g |
| | Tris buffer | 50 ml |
| (3) | preparation of dextran coated charcoal solution | |
| | Slowly dripped the dextran solution into charcoal solution with stirring. | |
| | Kept in refrigerator overnight. | |
| | Thirty minutes before use, kept it on ice with continuous mixing. | |
| | This solution could be kept in 4° C. for 2 month. | |

3. Tris buffer/Gelatin solution
    250 mg swine gelatin
    50 ml Tris buffer
    heated, stirred and cooled on ice.
    Prepared just before use.
4. DBP solution
    Human plasma was diluted to 1:5000 with Tris buffer/gelatin solution
5. Dilution of Standard 25(OH)D$_3$
    Stock 10,000 pg/50 μl
    Diluted to 0, 62.5, 125, 250, 500, 750, 1000, 10,000 pg/50 μl with ethanol
6. Dilution of Standard 1,25(OH)$_2$D$_3$
    Stock 200,000 pg/50 μl ($10^{-5}$ M/50 ul)
    Diluted to 6,250, 12,500, 25,000, 50,000, 100,000, 200,000 pg/50 III with ethanol
7. Dilution of test compounds
    Stock 200,000 pg/50 μl (10–3 M)
    Diluted to 12,500, 25,000, 50,000, 100,000, 200,000 and 400,000 pg/50 II with ethanol
8. [$^3$H-26,27]-25(OH)$_2$D$_3$ solution
    The stock solution was diluted in Tris buffer, 20,000 CPM/50 μl.

(C) Assay

| Label | 25(OH)D$_3$ | Test compounds (μl) | 3H-25(OH)D$_3$ (μl) | DBP (μl) | Supermix | Incubation (Rm T) | Charcoal dextran (μl) | On ice | Centrifuge | Counting |
|---|---|---|---|---|---|---|---|---|---|---|
| 1–3 (total) | — | — | 50 | — | 600 | — | — | | — | — |
| 4–8 | — | — | 50 | 500 | 600 | — | — | | — | — |
| STD 5–35 | 50 | — | 50 | — | | 4 h | 200 | 1 h | 2000 rpm 15 min, 4° C. | 200 μl Super + 600 μl Supermix |
| Test 36- | — | 50 | 50 | — | | | | | | |

(D) Calculation:

The amount of 25(OH)D$_3$ to displace 50 percent [$^3$H]-25(OH)D$_3$ is calculated as B$_{50}$ for 25(OH)D$_3$ DBP binding. The DBP binding of other compounds is calculated as B$_{50}$ relative to a value of 1 for 25(OH)D$_3$.

(E) Dilution of 25(OH)D$_3$:

| Amount (mol/50 ul) | From previous steps (μl) | Ethanol (μl) |
|---|---|---|
| 2.5 * 10$^{-11}$ (5 * 10$^{-7}$ M) | 5 * 10$^{-7}$ M | |
| 2.5 * 10$^{-12}$ | 40 | 360 |
| 1.875 * 10$^{-12}$ | 90 | 30 |
| 1.25 * 10$^{-12}$ | 130 | 130 |
| 6.25 * 10$^{-13}$ | 130 | 130 |
| 3.125 * 10$^{-13}$ | 130 | 130 |
| 1.5625 * 10$^{-13}$ | 130 | 130 |

(F) Dilution of 1, 25(OH)D$_3$

| Amount (mol in 50 μl) | From previous steps (μl) | Ethanol (μl) |
|---|---|---|
| 5 * 10$^{-10}$ (10$^{-5}$ M) | | |
| 2.5 * 10$^{-10}$ | 130 | 130 |
| 1.25 * 10$^{-10}$ | 130 | 130 |
| 6.25 * 10$^{-11}$ | 130 | 130 |
| 3.215 * 10$^{-11}$ | 130 | 130 |
| 1.625 * 10$^{-11}$ | 130 | 130 |

(G) Dilution of Test Compounds:

| Amount (mol in 50 μl) | From previous steps (μl) | Ethanol (μl) |
|---|---|---|
| Stock (10$^{-3}$ M) | | |
| 1.0 * 10$^{-9}$ | 5 | 245 |
| 5.0 * 10$^{-10}$ | 130 | 130 |
| 2.5 * 10$^{-10}$ | 130 | 130 |
| 1.25 * 10$^{-10}$ | 130 | 130 |
| 6.25 * 10$^{-11}$ | 130 | 130 |
| 3.125 * 10$^{-11}$ | 130 | 130 |

Figure 4:
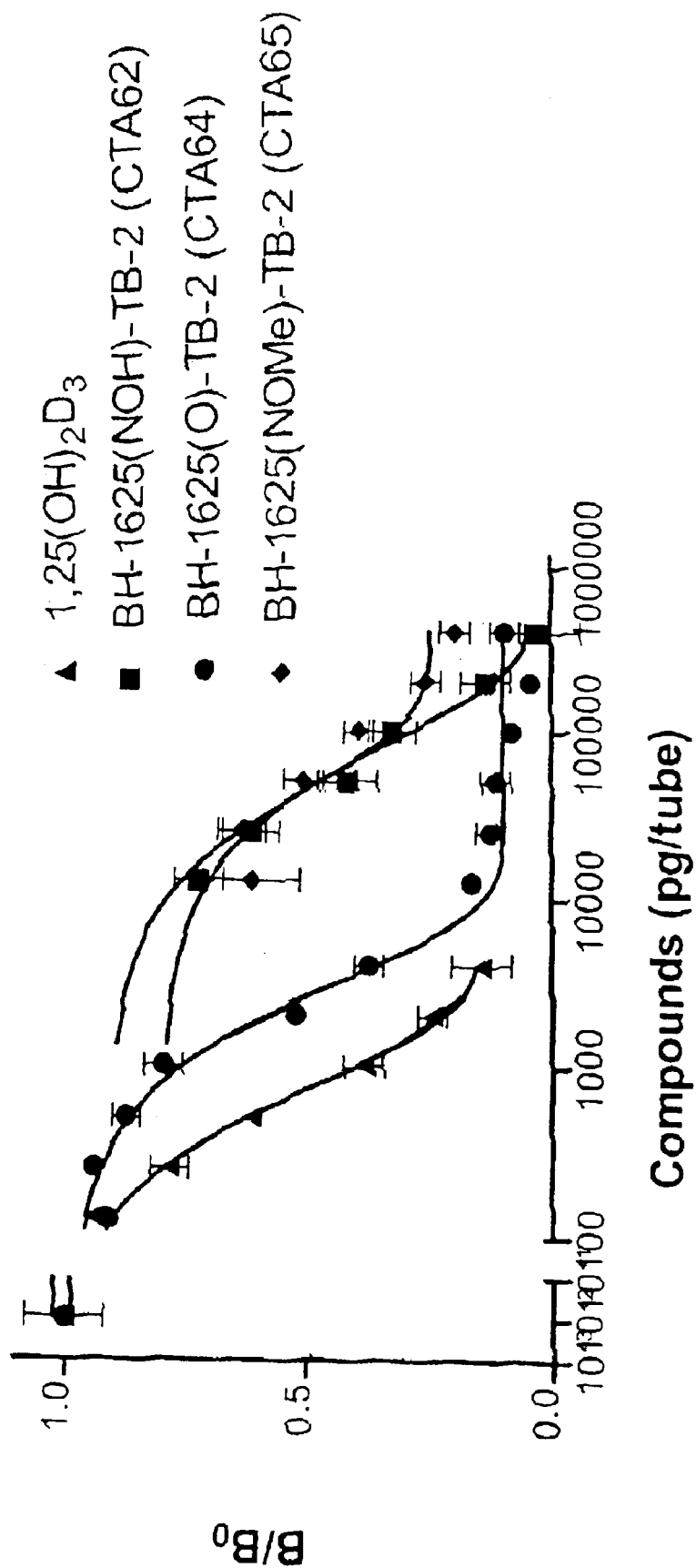
FIG. 4 is a graph showing the activity of compounds I(a) and I(c) (indicated as BH-1625(NOH)-TB-2 (CTA62) and BH-1625(NOMe)-TB-2-(CTA65) respectively) in the vitamin D receptor (VDR) binding assay compared to 1α,25-dihydroxy vitamin $D_3$.

(H) Results:

A graph showing the activity of compounds I(a) and I(c) (indicated as BH-1625(NOH)-TB-2 (CTA62) and BH-1625(NOMe)-TB-2-(CTA65) respectively) in the vitamin D receptor (VDR) binding assay compared to 1α,25-dihydroxy vitamin D$_3$ is shown in FIG. 4.

(I) References:

Bouillon R, van Baelen H, Moor P D. Comparative study of the affinity of the serum vitamin D-binding protein. (1980) J Steroid Biochem 13:1029–44.

Jones L, Byrnes B, Palma F, Segev D, Mazur E. Displacement potency of vitamin D$_2$ analogue in competitive protein-binding assay for 25-hydroxyvitamin D$_3$, 24,25-dihydroxyvitamin D$_3$ and 1,25-dihydroxyvitamin D$_3$ (1980) J Clin Endocrinol Metab 50:773–775

Example 13

Keratinocyte Proliferation

Compounds of Formula I(a) and I(c) were assayed in vitro for antiproliferative activity in murine keratinocytes using a standard protocol (Posner, G. H. et al. J. med. Chem. 1992, 35, 3280–3287). A graph showing the dose response effects of compounds I(a) and I(c) on keratinocyte proliferation in comparison to 1α,25-dihydroxy vitamin D$_3$ or calcitriol is shown in FIG. 5.

Example 14

Calcium Excretion

As a measure of their safety in animals, compound of Formula I(a) was administered orally to rats daily for 1 week at a similar dose (0.5 microgram/Kg body weight) to calcitriol, using a procedure described previously (Posner G. H. et al. J. Med. Chem. 1999, 42, 3425–3435). A graph showing the effect of compound I(a) (indicated as BH 1625(NOH)) on calcium levels in rat urine in comparison to calcitriol (1α,25-Dihydroxy vitamin D$_3$) is shown in FIG. 6.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A compound of Formula I, and pharmaceutically acceptable salts, hydrates, solvates, and prodrugs thereof:

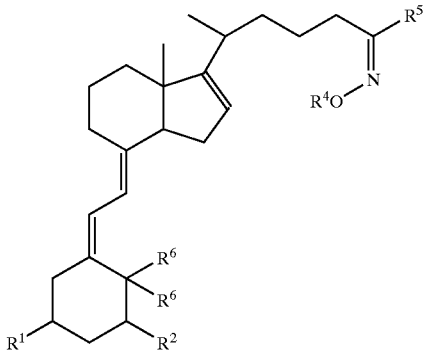

wherein
- $R^1$ and $R^2$ are independently selected from the group consisting of OH, $OC_{1-6}$alkyl, and halo;
- $R^3$ is $C_{1-6}$alkyl;
- $R^4$ is selected from the group consisting of H, $C_{1-6}$alkyl, aryl and heteroaryl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with aryl and heteroaryl being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$;
- $R^5$ is selected from the group consisting of $C_{1-6}$alkyl, cyclo($C_3$-$C_6$)alkyl, aryl and heteroaryl, aryl-$C_{1-6}$alkyl and heteroaryl-$C_{1-6}$alkyl, with $C_{1-6}$alkyl being unsubstituted or substituted with 1–4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl), and with cyclo($C_3$–$C_6$)alkyl, aryl, heteroaryl, aryl-$C_{1-6}$alkyl and heteroaryl-$C_{1-6}$alkyl, being unsubstituted or substituted with 1–5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O))OH, $C(O)OC_{1-4}$alkyl, $C(O)NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$; and
- $R^6$ are either both H or together from $=CH_2$.

2. The compound according to claim 1, wherein $R^1$ and $R^2$ are independently selected from the group consisting of OH, $OCH_3$, and fluoro.

3. The compound according to claim 2, wherein $R^1$ and $R^2$ are both OH.

4. The compound according to claim 1, wherein $R^3$ is $CH_3$.

5. The compound according to claim 1, wherein $R^4$ is selected from the group consisting of H, phenyl and $C_{1-4}$alkyl.

6. The compound according to claim 5, wherein $R^4$ is selected from the group consisting of H, phenyl, allyl and $CH_3$.

7. The compound according to claim 1, wherein $R^5$ is selected from the group consisting of isopropyl, s-butyl, t-butyl, and neopentyl.

8. The compound according to claim 7, wherein $R^5$ is t-butyl.

9. The compound according to claim 1, wherein the geometry about the C=N double bond of the oxime is trans.

10. The compound according to claim 1, wherein both $R^6$ are H.

11. The compound according to claim 1, having a relative stereochemistry as shown below:

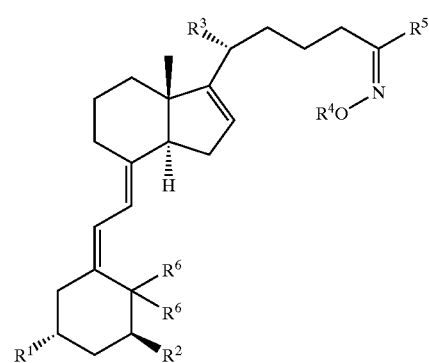

12. The compound according to claim 1 that is selected from the group consisting of:

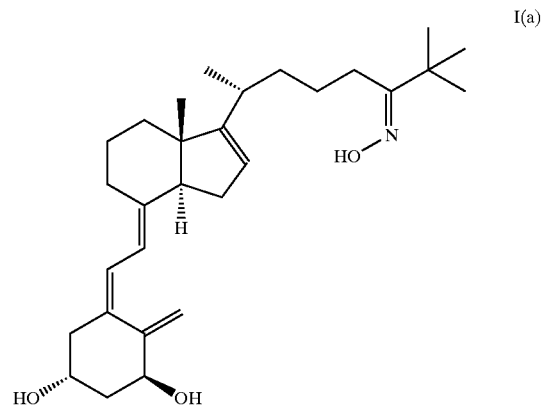

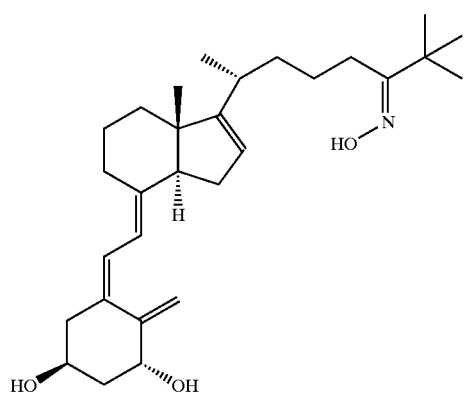
I(b)
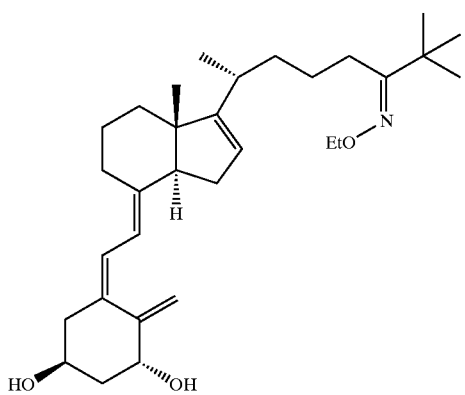
I(f)
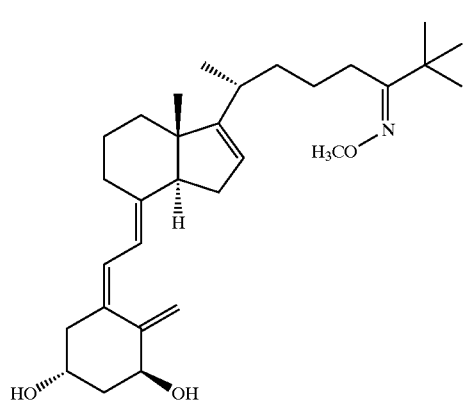
I(c)
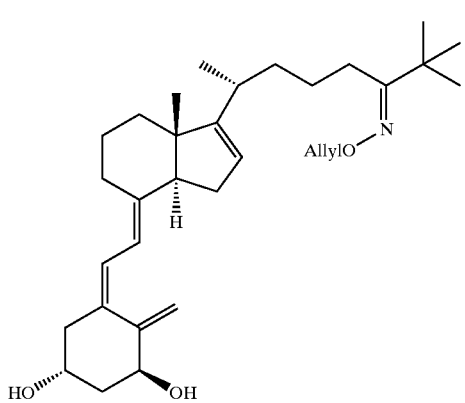
I(g)
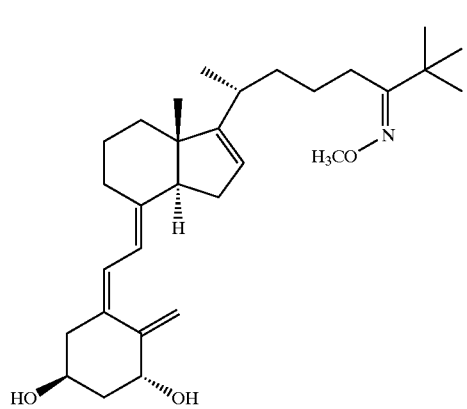
I(d)
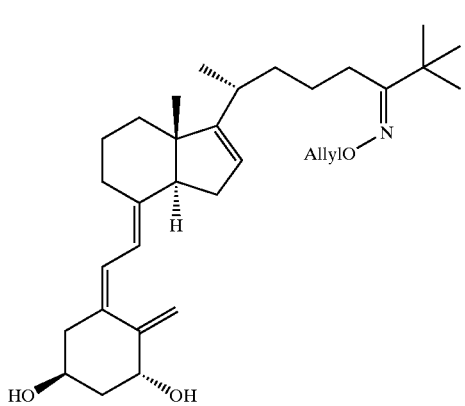
I(h)
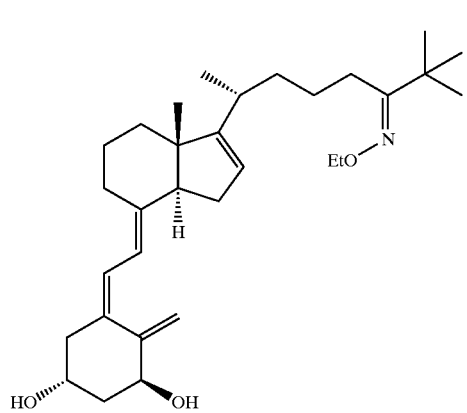
I(e)
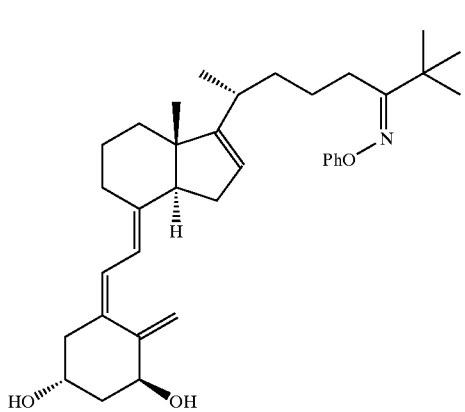
I(i)

-continued

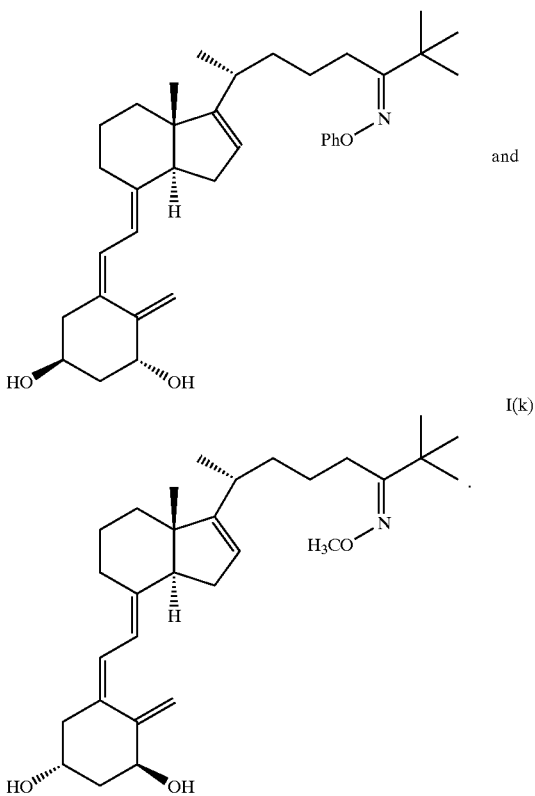

I(j)

and

I(k)

13. The compound according to claim 11 that is selected from the group consisting of compound I(a), I(c), I(e), I(g), I(i) and I(k).

14. A pharmaceutical composition comprising a compound according to claim 1 and a pharmaceutically acceptable carrier.

15. A method for treating diseases which benefit from a modulation of the levels of 1α,25-dihydroxy vitamin $D_3$ comprising administering an effective amount of a compound according to claim 1 to a cell or animal in need thereof.

16. A method for treating diseases which benefit from an inhibition of the catabolism of 1α,25-dihydroxy vitamin $D_3$ comprising administering an effective amount of a compound according to claim 1 to a cell or animal in need thereof.

17. The method according to claim 15, wherein the disease is selected from the group consisting of breast cancer, lung cancer, prostate cancer, dermatological disorders and bone disorders.

18. The method according to claim 17, wherein the disease is selected from the group consisting of breast cancer, lung cancer, prostate cancer, psoriasis and osteoporosis.

19. A method for inhibiting cell proliferation comprising administering an effective amount of a compound according to claim 1 to a cell or animal in need thereof.

20. The method according to claim 19, wherein the cell is a cancer cell.

21. The method according to claim 20, wherein the cancer is selected from breast cancer, lung cancer and prostate cancer.

22. A method of inhibiting CYP24 activity in a cell by administering an effective amount of a compound according to claim 1.

23. A method to modulate the levels of 1α,25-dihydroxy vitamin $D_3$ in an animal by administering a compound according to claim 1 to an animal in need thereof.

24. A method to inhibit the catabolism of 1α,25-dihydroxy vitamin $D_3$ in an animal by administering a compound according to claim 1 to an animal in need thereof.

25. A method to modulate the levels of 1α,25-dihydroxy vitamin $D_3$ in an animal by administering a pharmaceutical composition comprising a compound according to claim 1 to an animal in need thereof.

26. A method to inhibit the catabolism of 1α,25-dihydroxy vitamin $D_3$ in an animal by administering a pharmaceutical composition comprising a compound according to claim 1 to an animal in need thereof.

27. A method to inhibit cell proliferation in an animal by administering a compound according to claim 1 to an animal in need thereof.

28. A method to inhibit cell proliferation in an animal by administering a pharmaceutical composition comprising a compound according to claim 1 to an animal in need thereof.

29. A method to inhibit CYP24 activity in an animal by administering a compound according to claim 1 to an animal in need thereof.

30. A method to inhibit CYP24 activity in an animal by administering a pharmaceutical composition comprising a compound according to claim 1 to an animal in need thereof.

31. A method for increasing the efficacy of a vitamin D receptor agonist comprising co-administering an effective amount of a compound according to claim 1 and an effective amount of the vitamin D receptor agonist.

32. The method according to claim 21, wherein the vitamin D receptor agonist is 1α,25-dihydroxy vitamin $D_3$ (calcitriol).

33. A method to increase the efficacy of a vitamin D receptor agonist in an animal by administering a compound according to claim 1 to an animal in need thereof.

34. A method to increase the efficacy of a vitamin D receptor agonist in an animal by administering a pharmaceutical composition comprising a compound according to claim 1 to an animal in need thereof.

35. The method according to claim 33, wherein the vitamin D receptor agonist is 1α,25-dihydroxy vitamin $D_3$ (calcitriol).

36. The method according to claim 34, wherein the vitamin D receptor agonist is 1α,25-dihydroxy vitamin $D_3$ (calcitriol).

37. A method for preparing a compound of Formula I comprising reacting a compound of Formula II or salts, hydrates or solvates thereof

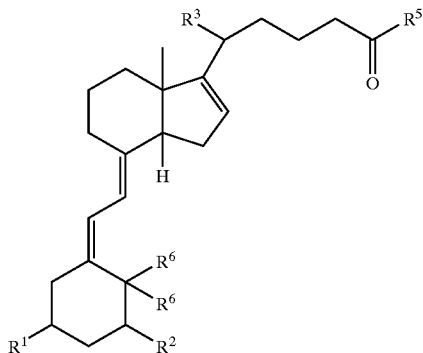

II with a compound of Formula III, or a salt, hydrate or solvate thereof:

$NH_2-OR^4$     III wherein

R$_1$ and R$_2$ are independently selected from the group consisting of OH, OC$_{1-6}$alkyl, OPG and halo; PG is a protecting group; R$^3$ in C$_{1-6}$alkyl;

wherein R$^4$ is selected from the group consisting of H, C$_{1-6}$alkyl, aryl and heteroaryl, with C$_{1-6}$alkyl being unsubstituted or substituted with 1–4 groups independently selected from C$_{1-4}$alkyl, OC$_{1-4}$alkyl, OH, halo, NH$_2$, NHC$_{1-4}$alkyl and N(C$_{1-4}$alkyl)(C$_{1-4}$alkyl) and with aryl and heteroaryl being unsubstituted or substituted with 1–5 groups independently selected from C$_{1-4}$alkyl, OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$, R$^5$ is selected from the group consisting of C$_{1-6}$alkyl, cyclo(C$_3$–C$_6$)alkyl, aryl and heteroaryl, aryl-C$_{1-6}$alkyl and heteroaryl-C$_{1-6}$alkyl, with C$_{1-6}$alkyl being unsubstituted or substituted with 1–4 groups independently selected from C$_{1-4}$alkyl, OC$_{1-4}$alkyl, OH, halo NH$_2$, NHC$_{1-4}$alkyl and N(C$_{1-4}$alkyl)(C$_{1-4}$alkyl), and with cyclo (C$_3$–C$_6$)alkyl, aryl, heteroaryl, aryl-C$_{1-6}$alkyl and heteroaryl-C$_{1-6}$alkyl, being unsubstituted or substituted with 1–5 groups independently selected from C$_{1-4}$alkyl, OC$_{1-4}$alkyl, OH, CF$_3$, OCF$_3$, halo, SH, SC$_{1-4}$alkyl, NH$_7$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$; and R$^6$ are either both H or together form =CH$_2$, in the presence of a non-nucleophilic amine; and removal of any protecting groups, if present.

38. The method according to claim 37, wherein the amine is pyridine.

39. The compound, according to claim 1 wherein the compound is:

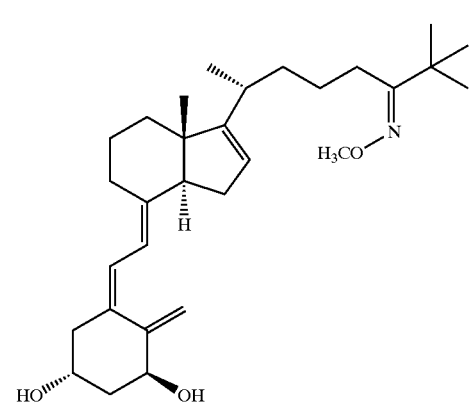

I(c)

40. The compound, according to claim 1 wherein the compound is:

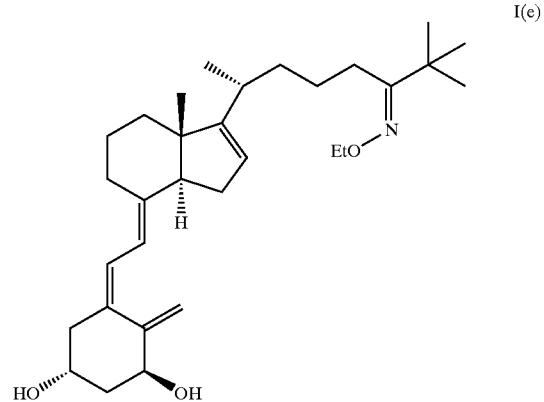

I(e)

41. The compound according to claim 1 wherein the compound is:

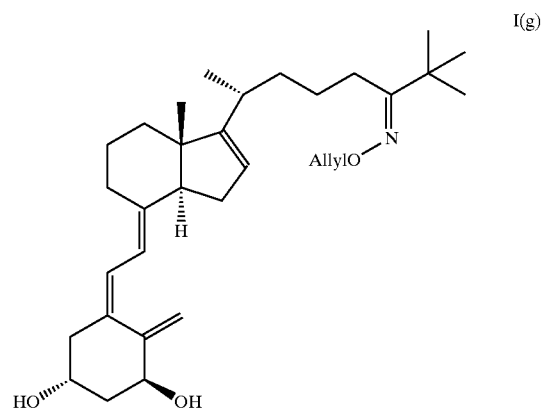

I(g)

42. The method according to claim 15, wherein the disease is selected from the group consisting of hyperparathyroidism, hypoparathyroidism, Pseudohypoparathyroidism, secondary hyperparathyroidism, diabetes, medullary carcinoma, psoriasis, wound healing, sarcoidosis, tuberculosis, chronic renal disease, hypophosphatemic VDRR, vitamin D dependent rickets, convulsion, fibrogenisis imperfecta ossium, osteitits fibrosa cystica, osteomalacia, osteoporosis, osteopenia, osteosclerosis, renal osteodystrophy and rickets.

* * * * *